(12) United States Patent
Diamant et al.

(10) Patent No.: US 8,801,875 B2
(45) Date of Patent: Aug. 12, 2014

(54) RADIOPAQUE ALLOY AND MEDICAL DEVICE MADE OF THIS ALLOY

(75) Inventors: Valery Diamant, Katsrin (IL); Dan Koren, Ramat Gan (IL); Alexander I. Lotkov, Tomsk (RU); Vladimir P. Sivokha, Tomsk (RU); Liydmila L. Meysner, Tomsk (RU); Viktor N. Grishkov, Tomsk (RU); Vladimir P. Voronin, Tomsk (RU)

(73) Assignees: Cook Medical Technologies LLC, Bloomington, IN (US); Lithotech Medical Ltd., Katrin (IL)

( * ) Notice: Subject to any disclaimer, the term of this patent is extended or adjusted under 35 U.S.C. 154(b) by 745 days.

(21) Appl. No.: 12/336,120

(22) Filed: Dec. 16, 2008

(65) Prior Publication Data
US 2009/0162243 A1   Jun. 25, 2009

Related U.S. Application Data

(60) Provisional application No. 61/016,055, filed on Dec. 21, 2007.

(51) Int. Cl.
| | |
|---|---|
| C22C 14/00 | (2006.01) |
| C22C 19/03 | (2006.01) |
| A61L 29/02 | (2006.01) |
| A61L 31/02 | (2006.01) |
| A61L 31/18 | (2006.01) |
| C22F 1/10 | (2006.01) |
| C22F 1/18 | (2006.01) |
| A61L 29/18 | (2006.01) |

(52) U.S. Cl.
CPC . *C22C 19/03* (2013.01); *C22F 1/10* (2013.01); *A61L 29/02* (2013.01); *A61L 31/18* (2013.01); *A61L 2400/16* (2013.01); *C22F 1/18* (2013.01); *A61L 31/022* (2013.01); *A61L 29/18* (2013.01); *C22C 14/00* (2013.01)

USPC .......... 148/402; 148/421; 148/426; 148/428; 420/417; 420/451; 420/459; 420/805

(58) Field of Classification Search
USPC .......... 148/402, 421, 426, 428; 420/417, 451, 420/459, 580
See application file for complete search history.

(56) References Cited

U.S. PATENT DOCUMENTS

| | | |
|---|---|---|
| RE28,681 E | 1/1976 | Baldwin |
| 4,865,663 A | 9/1989 | Tuominen et al. |

(Continued)

FOREIGN PATENT DOCUMENTS

| | | |
|---|---|---|
| EP | 0545612 A1 | 6/1993 |
| EP | 0783040 | 7/1997 |

(Continued)

OTHER PUBLICATIONS

The International Search Report and the Written Opinion of the International Searching Authority dated Mar. 19, 2009 for International Patent Application No. PCT/US2008/086994.

(Continued)

*Primary Examiner* — Sikyin Ip
(74) *Attorney, Agent, or Firm* — Brinks Gilson & Lione

(57) ABSTRACT

A radiopaque alloy based on titanium nickelide and having shape memory and superelastic properties includes, according to one embodiment, at least one radiopaque alloying element selected from among gold, platinum, and palladium at a concentration of from about 10 at. % to about 20 at. %, and at least one additional alloying element selected from among aluminum, chromium, cobalt, iron, and zirconium, where the additional alloying element has a concentration of from about 0.5 at. % to about 4 at. %. The alloy includes titanium at a concentration of from about 48 at. % to about 52 at. %, and the balance of the alloy is nickel. The radiopaque alloy preferably exhibits superelastic behavior suitable for medical device applications in the human body.

10 Claims, 20 Drawing Sheets

(56) References Cited

U.S. PATENT DOCUMENTS

| | | | |
|---|---|---|---|
| 5,001,446 A | 3/1991 | Tsuji et al. | |
| 5,069,226 A | 12/1991 | Yamauchi et al. | |
| 5,114,504 A * | 5/1992 | AbuJudom et al. | 148/402 |
| 5,230,348 A | 7/1993 | Ishibe et al. | |
| 5,636,641 A | 6/1997 | Fariabi | |
| 5,637,089 A | 6/1997 | Abrams et al. | |
| 5,641,364 A | 6/1997 | Golberg et al. | |
| 5,821,664 A * | 10/1998 | Shahinpoor | 310/307 |
| 5,885,381 A | 3/1999 | Mitose et al. | |
| 5,927,345 A | 7/1999 | Samson | |
| 5,951,793 A | 9/1999 | Mitose et al. | |
| 6,077,368 A | 6/2000 | Nakamura et al. | |
| 6,165,292 A * | 12/2000 | Abrams et al. | 148/563 |
| 6,277,084 B1 | 8/2001 | Abele et al. | |
| 6,312,454 B1 | 11/2001 | Stöckel et al. | |
| 6,312,455 B2 | 11/2001 | Duerig et al. | |
| 6,325,824 B2 | 12/2001 | Limon | |
| 6,352,515 B1 | 3/2002 | Anderson et al. | |
| 6,375,458 B1 | 4/2002 | Moorleghem et al. | |
| 6,399,886 B1 | 6/2002 | Avellanet | |
| 6,461,453 B1 | 10/2002 | Abrams et al. | |
| 6,482,166 B1 | 11/2002 | Fariabi | |
| 6,497,709 B1 | 12/2002 | Heath | |
| 6,557,993 B2 | 5/2003 | Rossin | |
| 6,569,194 B1 | 5/2003 | Pelton | |
| 6,572,646 B1 | 6/2003 | Boylan et al. | |
| 6,602,228 B2 | 8/2003 | Nanis et al. | |
| 6,626,937 B1 | 9/2003 | Cox | |
| 6,682,608 B2 | 1/2004 | Abrams et al. | |
| 6,706,053 B1 | 3/2004 | Boylan et al. | |
| 6,776,795 B2 | 8/2004 | Pelton | |
| 6,827,734 B2 | 12/2004 | Fariabi | |
| 6,830,638 B2 | 12/2004 | Boylan et al. | |
| 6,855,161 B2 | 2/2005 | Boylan et al. | |
| 6,884,234 B2 | 4/2005 | Aita et al. | |
| 6,904,310 B2 * | 6/2005 | Knapp et al. | 600/431 |
| 7,128,757 B2 | 10/2006 | Boylan et al. | |
| 7,192,496 B2 | 3/2007 | Wojcik | |
| 7,244,319 B2 | 7/2007 | Abrams et al. | |
| 7,258,753 B2 | 8/2007 | Abrams et al. | |
| 7,316,753 B2 | 1/2008 | Jung et al. | |
| 7,462,192 B2 | 12/2008 | Norton et al. | |
| 7,641,983 B2 | 1/2010 | Stinson | |
| 2002/0082681 A1 | 6/2002 | Boylan et al. | |
| 2003/0120181 A1 | 6/2003 | Toma et al. | |
| 2003/0193314 A1 | 10/2003 | Solingen | |
| 2004/0143317 A1 | 7/2004 | Stinson et al. | |
| 2004/0187980 A1 | 9/2004 | Jung et al. | |
| 2004/0220608 A1 | 11/2004 | D'Aquanni et al. | |
| 2004/0236409 A1 | 11/2004 | Pelton et al. | |
| 2004/0249447 A1 | 12/2004 | Boylan et al. | |
| 2005/0038500 A1 | 2/2005 | Boylan et al. | |
| 2005/0131522 A1 | 6/2005 | Stinson et al. | |
| 2005/0209683 A1 | 9/2005 | Yamauchi et al. | |
| 2006/0086440 A1 | 4/2006 | Boylan et al. | |
| 2006/0129166 A1 | 6/2006 | Lavelle | |
| 2006/0222844 A1 | 10/2006 | Stinson | |
| 2007/0249965 A1 | 10/2007 | Abrams et al. | |
| 2008/0114449 A1 | 5/2008 | Gregorich et al. | |

FOREIGN PATENT DOCUMENTS

| | | | |
|---|---|---|---|
| EP | 0873734 A2 | 10/1998 | |
| JP | 48 066521 A | 9/1973 | |
| JP | 58 157935 A | 9/1983 | |
| JP | 59 104459 A2 | 6/1984 | |
| JP | 61 210142 A2 | 9/1986 | |
| JP | 62 007839 A2 | 1/1987 | |
| JP | 9-137241 | 5/1997 | |
| JP | 11-036024 | 2/1999 | |
| JP | 11-106880 A * | 4/1999 | |
| WO | WO 01/72349 A1 | 10/2001 | |
| WO | WO 02/051462 A2 | 7/2002 | |
| WO | WO 03/088805 A2 | 10/2003 | |
| WO | WO 2004/033016 A1 | 4/2004 | |
| WO | WO 2005/102407 A1 | 11/2005 | |
| WO | WO 2006/066114 A1 | 6/2006 | |
| WO | WO 2006/081011 A2 | 8/2006 | |

OTHER PUBLICATIONS

Eckelmeyer, K.H. "The Effect of Alloying on the Shape Memory Phenomenon in Nitinol," *Scripta METALLURGICA*, 1976, 10, 667-672.

Noebe, R. "NiTi-Based High-Temperature Shape-Memory Alloys: Properties, Prospects, and Potential Applications," in *Advanced Structural Materials—Properties, Design Optimization, and Applications*, edited by Winston O. Soboyejo, CRC Press, 2006, Boca Raton, FL USA, 145-186.

Van Humbeeck, J. "Shape Memory Alloys," in *Smart Materials*, edited by Mel Schwartz, CRC Press, 2008, Boca Raton, FL, USA, 20-28 to 20-36.

Yang, W.S.; Mikkola, D.E. "Ductilization of TiNi—Pd Shape Memory Alloys with Boron Additions," *Scripta METALLURGICA*, 1993, 28, 161-165.

International Preliminary Report on Patentability for International Patent Application No. PCT/US2007/019445 dated Dec. 4, 2008.

The International Search Report and the Written Opinion for International Patent Application No. PCT/US2007/019445 dated Dec. 14, 2007.

"Biological Evaluation of Medical Devices—Part 1: Evaluation and Testing," *American National Standard ANSI/AAMI/ISO 10993-1:2003*, Association for the Advancement of Medical Instrumentation (AAMI), Arlington, VA, USA, 2003, 25 pages.

"Radiopaque Polymers," *Encyclopedia of Polymer Science and Engineering*, John Wiley & Sons, Inc., New York, USA, 1988, 14, pp. 1-8 (10 pages).

"Standard Practice for Direct Contact Cell Culture Evaluation of Materials for Medical Devices," *American Society for Testing and Materials (ASTM) Standard F813-01*, ASTM International, West Conshohocken, PA, 2001, 4 pages.

"Standard Practice for Selecting Generic Biological Test Methods for Materials and Devices," *American Society for Testing and Materials (ASTM) Standard F748-04*, ASTM International, West Conshohocken, PA, 2004, 7 pages.

"Standard Specification for Wrought Nickel-Titanium Shape Memory Alloys for Medical Devices and Surgical Implants," *American Society for Testing and Materials (ASTM) Standard F2063-05*, ASTM International, West Conshohocken, PA, 2005, 4 pages.

"Standard Test Method for Agar Diffusion Cell Culture Screening for Cytotoxicity," *American Society for Testing and Materials (ASTM) Standard F895-84*, ASTM International, West Conshohocken, PA, 2006, 5 pages.

"Standard Test Method for Tension Testing of Nickel-Titanium Superelastic Materials," *American Society for Testing and Materials (ASTM) Standard F2516-07*, ASTM International, West Conshohocken, PA, 2007, 6 pages.

"Standard Test Method for Transformation Temperature of Nickel-Titanium Alloys by Thermal Analysis," *American Society for Testing and Materials (ASTM) Standard F2004-05*, ASTM International, West Conshohocken, PA, 2005, 4 pages.

Aichinger, H.; Dierker, J.; Joite-Barfuβ, S.; Säbel, M. "Raw X-Ray Data for Unfiltered Photons," *Radiation Exposure and Image Quality in X-Ray Diagnostic Radiology: Physical Principles and Clinical Applications*, Springer, Berlin.

Boriskina, N.G.; Kenina, E.M. "Phase Equilibria in the Ti—TiPd—TiNi System Alloys," *Titanium '80, Science and Technology, Proceedings of the 4th Intrnational Conference on Titanium*, Kumura, H. and Izumi O., eds., 1980, The Metallurgical Society of AIME, Warrendale, PA, pp. 2917-2927.

Bozzolo, G.; Noebe, R.D.; Mosca, H.O. "Atomistic Modeling of Pd Site Preference in NiTi," *Journal of Alloys and Compounds*, 2005, 386, pp. 125-138.

Cai, W.; Tanaka, S.; Otsuka, K. "Thermal Cyclic Characteristics Under Load in a $Ti_{50.6}Pd_{30}Ti_{19.4}$ Alloy," *Materials Science Forum*, 2000, 327-328, pp. 279-282.

(56) References Cited

OTHER PUBLICATIONS

Cai, W.; Zhao, L. "The Reverse Transformation of Deformation-Induced Martensite in a Ni—Ti—Nb Shape Memory Alloy with Wide Hysteresis," *Shape Memory Materials'94 Proceedings of the International Symposium on Shape Memory Materials*, 1994, International Academic Publishers, pp. 235-238 (5 pages).

Craig, C.; Friend, C.; Edwards, M.; Gokcen, N. "Tailoring Radiopacity of Austenitic Stainless Steel for Coronary Stents," *Proceedings from the Materials & Processes for Medical Devices Conference*, Sep. 8-10, 2003, ASM International, Anaheim, CA, 2004, pp. 294-297.

Di, J.; Wenxi, L.; Ming, H.; Defa, W.; Zhizhong, D. "Some Properties of Ni—Ti—Nb—X Quarternary Alloys," *Z. Metallkd.*, 2000, 91(3), pp. 258-260.

Donkersloot, H.C.; Van Vucht, J.H.N. "Martensitic Transformations in Gold—Titanium, Palladium—Titanium and Platinum—Titanium Alloys Near the Equiatomic Composition," *Journal of the Less-Common Metals*, 1970, 20, pp. 83-91.

Enami, K.; Nara, M.; Maeda, H. "Effect of W Addition on the Martensitic Transformation and Shape Memory Behaviour of the TiNi-Base Alloys," *Journal de Physique IV*, 1995, 5, pp. C8-629-C8-633.

Enami, K.; Yoshida, T.; Nenno, S. "Premartensitic and Martensitic Transformations in TiPd—Fe Alloys," *Proceedings of the International Conference on Martensitic Transformations*, The Japan Institute of Metals, 1986, pp. 103-108.

Golberg, D.; Xu, Y.; Murakami, Y.; Otsuka, K.; Ueki, T.; Horikawa, H. "High-Temperature Shape Memory Effect in $Ti_{50}Pd_{50-x}Ni_x$ (x=10, 15, 20) Alloys," *Materials Letters*, 1995, 22, pp. 241-248.

Gschneidner Jr., K.; Russell, A.; Pecharsky, A.; Morris, J.; Zhang, Z.; Lograsso, T.; Hsu, D.; Chester Lo, C.H.; Ye, Y.; Sieger, A.; Kesse, D. "A Family of Ductile Intermetallic Compounds," *Nature Materials*, 2003, 2, pp. 587-590.

Gupta, K.P. "The Hf—Ni—Ti (Hafnium—Nickel—Titanium) System," *Journal of Phase Equilibria*, 2001, 22(1), pp. 69-72.

Hashi, K.; Ishikawa, K.; Matsuda, T.; Aoki, K. "Hydrogen Permeation Characteristics of Multi-Phase Ni—Ti—Nb Alloys," *Journal of Alloys and Compounds*, 2004, 368, pp. 215-220.

Hashi, K.; Ishikawa, K.; Matsuda, T.; Aoki, K. "Hydrogen Permeation of Ternary Ni—Ti—Nb Alloys," *Advanced Material for Energy Conversion II*, 2004, TMS (The Minerals, Metals & Material Society), Warrendale, PA, pp. 283-289.

Haxel, G.B.; Hedrick, J.B.; Orris, G.J. "Rare Earth Elements-Critical Resources for High Technology," USGS Fact Sheet 087-02, U.S. Dept. of the Interior, 2002, 4 pages.

Hodgson, D.E.; Brown, J.W. *Using Nitinol Alloys*, Shape Memory Applidations, Inc., San Jose, CA, 2000, 52 pages.

Hosoda, H.; Tsuji, M.; Takahashi, Y.; Inamura, T.; Wakashima, K.; Yamabe-Mitarai, Y.; Miyazaki, S.; Inoue, K. "Phase Stability and Mechanical Properties of Ti—Ni Shape Memory Alloys containing Platinum Group Metals," *Materials Science Forum*, 2003, 426-432, pp. 2333-2338.

Huang, X.; Lei Y.; Huang, B.; Chen, S.; Hsu, T.Y. "Effect of Rare-Earth Addition on the Shape Memory Behavior of a FeMnSiCr Alloy," *Materials Letters*, 2003, 57, pp. 2787-2791.

Huisman-Kleinherenbrink, P.M.; Beyer, J. "The Influence of Ternary Additions on the Transformation Temperatures of NiTi Shape Memory Alloys—A Theoretical Approach," *Journal de Physique IV*, 1991, 1, pp. C4-47-C4-52.

Jung, J.; Ghosh, G.; Olson, G.B. "A Comparative Study of Preciptiation Behavior of Heusler Phase ($Ni_2TiAl$) from B2-TiNi in Ni—Ti—Al and Ni—Ti—Al-X (X = Hf, Pd, Pt, Zr) Alloys," *Acta Materialia*, 2003, 51, pp. 6341-6357.

Kattner, U.R. "Thermodynamic Modeling of Multicomponent Phase Equilibria," *Journal of Metals (JOM)*, 1997, 49(12), pp. 14-19.

Khachin, V.N.; Gjunter, V.E.; Sivokha, V.P.; Savvinov, A.S. "Lattice Instability, Martensitic Transformations, Plasticity and Anelasticity of TiNi," *Proc. ICOMAT*, 1979, 79, pp. 474-479.

Khachin, V.N.; Matveeva, N.M.; Sivokha, V.P.; Chernov, D.B.; Kovneristyi, Y.K. "High-Temperature Shape-Memory Effects in Alloys of the TiNi—TiPd System," Translated from Doklady Akademii Nauk SSSR, vol. 257, No. 1, pp. 167-169, Mar. 1981. Plenum Publishing Corporation, New York, NY, 1981, pp. 195-197.

Lindquist, P.G. "Structure and Transformation Behavior of Martensitic Ti—(Ni, Pd) and Ti—(Ni, Pt) Alloys,"0 University Microfilms International, Ann Arbor, MI, 1988, Order No. 8908756, 134 pages.

Lindquist, P.G.; Wayman, C.M. "Shape Memory and Transformation Behavior of Martensitic Ti—Pd—Ni and Ti—Pt—Ni Alloys," *Engineering Aspects of Shape Memory Alloys*, Butterworth-Heinemann, Ltd., London, UK, 1990, pp. 58-68.

Liu, A.; Meng, X.; Cai, W.; Zhao, L. "Effect of Ce Addition on Martensitic Transformation Behavior of TiNi Shape Memory Alloys," *Materials Science Forum*, 2005, 475-479, pp. 1973-1976, 6 pages.

Liu, A.L.; Gao, Z.Y.; Gao, L.; Cai, W.; Wu, Y. "Effect of Dy Addition on the Microstructure and Martensitic Transformation of a Ni-rich TiNi Shape Memory Alloy," *Journal of Alloys and Compounds*, 2007, 437, pp. 339-343.

Liu, J.; Ma, J.; Wang, Z.; Wu, G. "Effects of Aging Treatment on Shape Memory Characteristics of Ni—Ti—Ta Alloy," *Rare Metal Materials and Engineering*, 2003, 32(10), pp. 777-781 (6 pages).

Liu, J.; Pan, S.; Zhuang, Y. "Isothermal Section of the Phase Diagram of the Ternary System Dy—Ni—Ti at 773 K," *Journal of Alloys and Compounds*, 2000, 313, pp. 93-94.

Liu, M.; Tu, M.J.; Zhang, X.M.; Li, Y.Y.; Shelyakov, A.V. "Microstructure of Melt-Spinning High Temperature Shape Memory Ni—Ti—Hf Alloys," *Journal of Materials Science Letters*, 2001, 20, pp. 827-830.

Ma, J.; Liu, J.; Wang, Z.; Xue, F.; Wu, K-H.; Pu, Z. "Effects of Ta Addition on NiTi Shape Memory Alloys," *J. Mater. Sci. Technol.*, 2000, 16(5), pp. 534-536.

Ma, J.; Yang, F.; Subirana, J.I.; Pu, Z.J.; Wu; K.H. "Study of NiTi—Ta Shape Memory Alloys," *SPIE Conference on Smart Materials Technologies*, 1998, 3324, pp. 50-57.

Meisner, L.L.; Sivokha, V.P. "The Effect of Applied Stress on the Shape Memory Behavior of TiNi-Based Alloys with Different Consequences of Martensitic Transformations," *Physica B*, 2004, 344, pp. 93-98.

Noebe, R.; Gaydosh, D.; Padula, S.; Garg, A.; Biles, T.; Nathal, M. "Properties and Potential of Two (Ni,Pt)Ti Alloys for Use as High-Temperature Actuator Materials," $12^{th}$ *SPIE Conf. International Symposium*, San Diego, CA, USA, Mar. 6-10, 2005, pp. 1-12.

Otsuka, K.; Oda, K.; Ueno, Y.; Piao, M.; Ueki, T.; Horikawa, H. "The Shape Memory Effect in a $Ti_{50}Pd_{50}$ Alloy," *Scripta Metallurgica et Materialia*, 1993, 29, pp. 1355-1358.

Oyamada, O.; Amano, K.; Enomoto, K., Shigenaka, N.; Matsumoto, J.; Asada, Y. "Effect of Environment on Static Tensile and Fatigue Properties of Ni—Ti—Nb Shape Memory Alloy," *JSME International Journal*, 1999, Series A, 42, pp. 243-248.

Pryakhina, L.I.; Myasnikova, K.P.; Burnashova, V.V.; Cherkashin, E.E.; Markiv, V.Y. "Ternary Intermetallic Compounds in the System Ni—Ti—Nb," A. A. Baikov Institute of Metallurgy; (Translated from *Poroshkovaya Metallurgiya*, 1966, 8(44), pp. 61-69) pp. 643-650.

Qiang, D.S.; Ying, Q.G.; Bo, Y.H.; Ming, T.S. "Phase Transformation and Memory Effect of the High Temperature Shape Memory Alloy $Ti_{49}Ni_{25}Pd_{26}B_{0.12}$," *Shape Memory Materials'94 Proceedings of the International Symposium on Shape Memory Materials*, 1994, International Academic Publishers, Beijing, China, pp. 248-252 (6 pages).

Rios, O.; Noebe, R.; Biles, T.; Garg, A.; Palczer, A.; Scheiman, D.; Seifert, H.J.; Kaufman, M. "Characterization of Ternary NiTiPt High-Temperature Shape Memory Alloys," $12^{th}$ *SPIE Conf. International Symposium*, San Diego, CA, USA, Mar. 6-10, 2005, pp. 1-12.

Russell, S.M.; Hodgson, D.E.; Basin, F. "Improved NiTi Alloys for Medical Applications,". *SMST-97: Proceedings of the Second International Conference on Shape Memory and Superelastic Technologies*, Pacific Grove, CA, 1997, pp. 429-436.

Seo, C-Y.; Choi, S-J.; Choi, J.; Park, C-N.; Lee, P.S.; Lee, J-Y. "Effect of Ti and Zr Additions On the Characteristics of $AB_5$-type Hydride Electrode for Ni-MH Secondary Battery," *International Journal of Hydrogen Energy*, 2003, 28, 317-327.

(56) References Cited

OTHER PUBLICATIONS

Shimizu, S.; Xu, Y.; Okunishi, E.; Tanaka, S.; Otsuka, K.; Mitose, K. "Improvement of Shape Memory Characteristics by Precipitation-Hardening of Ti—Pd—Ni Alloys," *Materials Letters*, 1998, 34, pp. 23-29.

Stoeckel, D. "Shape Memory Actuators for Automotive Applications," *Materials & Design*, 1990, 11, pp. 302-307.

Sun, L.; Wu, K-H. "The Two-Way Memory Effect (TWME) in NiTi—Pd High Temperature Shape Memory Alloys," *SPIE Conference Proceedings: Smart Structures and Materials*, 1994, 2189, pp. 298-305.

Suzuki, Y.; Xu, Y.; Morito, S.; Otsuka, K.; Mitose, K. "Effects of Boron Addition on Microstructure and Mechanical Properties of Ti—Pd—Ni High-Temperature Shape Memory Alloys," *Materials Letters*, 1998, 36, pp. 85-94.

Thoma, P.E.; Boehm, J.J. "The Effect of Hafnium and Thermal Cycling on the Transformation Temperatures of NiTi-Based Shape Memory Alloys," *Mat. Res. Soc. Symp. Proc.*, 2000, 604, pp. 221-226.

*Using Nitinol Alloys*, Johnson Matthey, San Jose, CA, 2004, 1-46.

Wong, T.; Seuntjens, J.M.; "Development of Rare Earth Regenerator Materials in Fine Wire Form," *Adv. Cryog. Eng.*, 1997, 42, pp. 439-444, 2 pages Abstract.

Wu, K.H.; Liu, Y.Q.; Maich, M.; Tseng, H.K. "The Mechanical Properties of a NiTi—Pd High Temperature Shape Memory Alloy," *SPIE Conference Proceedings: Smart Structures and Materials*, 1994, 2189, pp. 306-313.

Wu, S.K.; Wayman, C.M. "Martensitic Transformations and the Shape Memory Effect in $Ti_{50}Ni_{10}Au_{40}$ and $Ti_{50}Au_{50}$ Alloys," *Metallography*, 1987, 20, pp. 359-376.

Wu, T. Wu, M.H. "NiTiNb Plugs for Sealing High Pressure Fuel Passages in Fuel Injector Appliations," *Proceedings, International Conference on Shape Memory and Superelastic Technologies (SMST-2000)*, 2000, Pacific Grove, CA, pp. 235-240.

Xu, Y.; Otsuka, K.; Furubayashi, E.; Mitose, K. "TEM Observation of Recrystallization Process in Solution-Treated $Ti_{50}Pd_{50}$ Martensite," *Materials Letters*, 1998, 34, pp. 14-18.

Xu, Y.; Shimizu, S.; Suzuki, Y.; Otsuka, K.; Ueki, T.; Mitose, K. "Recovery and Recrystallization Processes in Ti_Pd_Ni High-Temperature Shape Memory Alloys," *Acta Mater.*, 1997, 45(4), pp. 1503-1511.

Zadno, G.R.; Duerig, T.W. "Linear Superelasticity in cold-worked Ni—Ti," *Engineering Aspects of Shame Memory Alloys*, Butterworth-Heinemann, Ltd., 1990, pp. 414-419.

Zhang, C.; Thoma, P.; Chin, B.; Zee, R. "Martensitic and R-Phase Transformations in Ni—Ti and Ni—Ti—Hf," *Trans. Nonferrous Met. Soc. China*, 1999, 9(1), pp. 55-64.

Zhao, C. "Improvement of Shape Memory Effect in Fe—Mn—Si—Cr—Ni Alloys," *Metallurgical and Materials Transactions A*, 1999, 30A, pp. 2599-2604.

Zhu, Y.R.; Pu, Z.J.; Li, C.; Wu, K.H. "The Stability of NiTi—Pd and NiTi—Hf High Temperature Shape Memory Alloys," *Shape Memory Materials '94 Proceedings of the International Symposium on Shape Memory Materials*, 1994, International Academic Publishers, pp. 253-257 (6 pages).

Khachin, V.N., "Martensitic Transformation and Shape Memory Effect in B2 Intermetallic Compounds of Titanium," *Review Phys. Appl.* 24 (1989) pp. 733-739.

Meisner, L.L., & Sivokha, V.P., "Physical and Biochemical Principles of the Application of TiNi-Based Alloys as Shape Memory Implants," in Yahia, L. (ed.) *Shape Memory Implants*, Springer Verlag Berlin Heidelberg, Germany (2000) pp. 61-71.

Khachin, V.N., Pushin, V.G., & Kondratiev, V.V., *Titanium Nickelid. Structure and Properties*, Moscow.-Nauka. (1992) 5 pages. (English Language).

Sivokha V.P., Khachin V.N., "Martensitic Transformation and Shape Memory Effect in Alloys of TiNi—TiAu System,"*AVV*, 62, 3 (1986). pp. 533-540 (English Language).

US 5,976,281, 11/1999, Nakamura et al. (withdrawn)

\* cited by examiner

Exemplary X-ray pictures (samples diameter ~ 200 μkm) alloy TiNi, with radiopaque elements (at. %) – Pd: 1 – 10, 2 – 25, 3 – 30, 4 – 35; Au: 5 – 8, 6 – 14, 7 – 35; Pt: 8 – 12, 9 – 35.

RADIOPAQUE ALLOY AND MEDICAL DEVICE MADE OF THIS ALLOY

RELATED APPLICATION

The present patent document claims the benefit of the filing date under 35 U.S.C. §119(e) of U.S. Provisional Patent Application Ser. No. 61/016,055, which was filed on Dec. 21, 2007, and is hereby incorporated by reference in its entirety.

FIELD OF THE INVENTION

This invention is generally in the field of metallurgy, and more specifically relates to radiopaque alloys and medical devices comprising these alloys.

BACKGROUND OF THE INVENTION

Shape memory alloys (SMAs) are the group of metallic materials that exhibit a shape-memory effect (SME). The shape-memory effect is the ability to return to a previously defined shape through an appropriate thermal procedure after being severely deformed, and is a consequence of a crystallographic reversible, thermoelastic martensitic transformation (TMT). In martensitic transformations, there exists a parent, high-temperature austenite crystallographic phase having higher symmetry. As the temperature lowers, the crystallographic structure changes to martensite, a phase with lower symmetry. It is possible for multiple variants or orientations of the martensite phase to be present in the same material.

Phase transformations between austenite and martensite exhibit a hysteresis and can be activated by either temperature or stress. FIG. 1 and FIG. 2 schematically illustrate the forward and reverse phase transformations in the strain-temperature ($\epsilon$-T) plane and in the stress-strain ($\sigma$-$\epsilon$) plane, respectively.

Specifically, transformation through a thermocycle is illustrated in FIG. 1, where $M_s$ (martensite start temperature) is the temperature at which martensite formation begins, $M_f$ (martensite finish temperature) is that at which martensite formation terminates, $A_s$ (austenite start temperature) is that at which the reverse transformation begins, and $A_f$ (austenite finish temperature) is that at which the reverse transformation terminates. When a SMA is heated above $A_s$, the martensite variants change to reproduce the shape of the parent phase.

FIG. 2 corresponds to the case when an exemplary SMA is deformed at a constant temperature. This temperature is preferably in the range between $A_f$ and $M_d$ where $A_f$ is the previously defined austenite finish temperature, and $M_d$ marks the maximum temperature at which martensite can be induced by an applied stress without substantially plastically deforming the austenite phase. With an increase in stress level (analogous to a decrease in temperature in the previous case), the martensite phase starts to form in the material. The line from point A to point B represents the elastic deformation of a SMA. After point B, the strain or deformation is no longer proportional to the applied stress, and it is in the region between point B and point C that the stress-induced transformation of the austenitic phase to the martensitic phase begins to occur. There also can be an intermediate phase, called the rhombohedral phase (or more commonly, the "R-Phase"), depending upon the composition and the thermomechanical history of the alloy. At point C moving toward point D, the material enters a region of relatively constant stress with significant deformation or strain. This constant stress region is known as the loading plateau, and it is in this plateau region C-D that the transformation from austenite to martensite occurs.

At point D the transformation to the martensitic phase due to the application of stress to the specimen is substantially complete. Beyond point D the martensitic phase begins to deform, elastically at first, but, beyond point E, the deformation is plastic.

When the stress applied to the superelastic metal is removed, the material behavior follows the curve from point E to point F. Within the E to F region, elastic recovery occurs. At point F in the recovery process, the metal begins to transform from the metastable, martensitic phase back to the more stable austenitic phase.

In the region from point G to point H, which is also an essentially constant or plateau stress region, the phase transformation from martensite back to austenite takes place. This constant stress region G-H is known as the unloading plateau. The line from point I to the starting point A represents the elastic recovery of the metal to its original shape.

The ability to incur significant strain under an applied stress and to recover from the deformation upon removal of the load is commonly referred to as "superelasticity" and sometimes "pseudoelasticity." In an ideal system, superelastic behavior is characterized by regions of nearly constant stress upon loading and unloading, identified above as loading plateau stress C-D and unloading plateau stress G-H.

Numerous alloys having shape memory effect and superelasticity are known, such as silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc (Cu—Zn), copper-zinc-aluminum (Cu—Zn—Al), copper-zinc-tin (Cu—Zn—Sn), copper-zinc-xenon (Cu—Zn—Xe), iron beryllium ($Fe_3Be$), iron platinum ($Fe_3Pt$), indium-thallium (In—Tl), iron-manganese (Fe—Mn), nickel-aluminum (Ni—Al), copper based alloys, as well as Ni—Ti (nickel-titanium) based alloys. Moreover, equiatomic or near-equiatomic nickel-titanium alloys (i.e., Nitinol) are very important for practical uses owing to their physical, mechanical and chemical properties, performance specifications, corrosion resistance and SME. In particular, Ti—Ni alloys can exhibit 50-60% elongation and have a tensile strength up to 1000 MPa. Upon heat treatment, Ti—Ni transforms from a ductile martensite phase with B19' structure to a stiffer austenite phase of B2 structure. When cooled, Ti—Ni shifts in structure from B2 to B19'. In bulk equiatomic Ti—Ni, $M_s$ is approximately within the range of 60° C.-65° C., and $A_s$ is approximately 95° C.-100° C. These transformation temperatures, however, can be significantly lower for thin films and are highly dependent on composition and residual stresses. The martensitic transformations depend on the chemical composition of the alloy. Thus, when Nitinol is alloyed with other metals, cooling of the material can provide transformation of B2 structure to either B19 structure or to the so-called R-phase, and then to the B19' structure.

SMAs may be practically used for actuators, pipe couplings, switches or the like by taking advantages of their shape memory properties. Products that rely on the superelasticity of the SMAs include, but are not limited to, antennas, eye glass frames, wires of brassieres, orthodontic archwires, etc. Various proposals have also been made to employ SMAs in the medical field. For example, U.S. Pat. No. 3,620,212 to Fannon et al. proposes the use of an SMA intrauterine contraceptive device, U.S. Pat. No. 3,786,806 to Johnson et al. proposes the use of an SMA bone plate, U.S. Pat. No. 3,890,977 to Wilson proposes the use of an SMA element to bend a catheter or cannula, etc. In this connection, the functional capabilities of nickel-titanium alloys are especially important in medicine because their biochemical properties best match the mechanical behavior and properties of human living tissues. Various nickel-titanium alloys can also be used in guide wires, cardiac pacing leads, sutures, prosthetic implants, such as stents, intraluminal filters, retrieval baskets, aneurysm clips, bone plates and screws, femoral fixation devices, intramedullary nails and pins, and joints for ankles, elbows, fingers, knees, hips, shoulders and wrists. Such nickel-titanium alloys are described in, for example, U.S. Pat. Appl. Pub. Nos. 2001/0001317 to Duerig et al., 2004/0249447 and 2006/0086440 to Boylan et al., 2004/0143317 to Stinson, 2004/0236409 to Pelton et al., 2004/220608 to Wayne et al., 2005/209683 to YAMAUCHI, U.S. Pat. No. 5,951,793 to Mitose et al., U.S. Pat. No. 6,312,455 to Duerig et al., U.S. Pat. No. 6,306,141 to Jervis, U.S. Pat. No. 6,676,700 to Jacobs et al., U.S. Pat. No. 6,926,733 to Stinson, U.S. Pat. No. 6,776,795 to Pelton et al., U.S. Pat. No. 6,855,161 to Boylan et al.).

Although nickel-titanium alloys are useful and valuable to the medical field, one of the disadvantages of the medical implants made of the known SMAs is the fact that they are not sufficiently radiopaque, as compared to, for example, devices made of medical stainless steel.

The radiopacity of medical implants can be improved in several ways. For example, virtually regardless of the energy and wavelength of incident x-rays, material having a high mass per unit of illuminated area (material density) is radiopaque; indeed, the radiopacity of high mass constructions is generally higher than that of low mass constructions. However, the extensive use in medical practice of small-size articles made from materials having SME and superelasticity imposes limits on the utilization of high mass constructions.

Radiopacity can also be improved through coating processes such as sputtering, plating, or co-drawing high radiopacity metals onto the medical device. These processes, however, may create complications such as material compatibility, galvanic corrosion, coating adhesion or delamination, biocompatibility, etc.

Radiopacity can also be improved by alloy addition. A challenge for medical device applications is the preparation of a suitably radiopaque Ti—Ni alloy that also displays superelastic behavior around body temperature. It would be advantageous to develop a radiopaque nickel-titanium alloy that provides a substantial improvement in radiopacity compared to binary Ti—Ni alloys without a loss in superelastic properties.

SUMMARY OF THE INVENTION

Described herein is a radiopaque nickel-titanium alloy that may provide increased radiopacity compared to binary Ti—Ni alloys. The radiopaque alloy preferably displays superelastic behavior and shape memory properties suitable for medical device applications in the human body. Also disclosed herein is a medical device comprising the radiopaque nickel-titanium alloy.

According to one embodiment, the alloy comprises at least one radiopaque alloying element to provide a desired radiopacity of the alloy. The alloy further comprises at least one additional alloying element to maintain the superelasticity properties of the alloy within a desired superelasticity temperature interval. The alloy may also comprise at least one further alloying element to provide instability of the alloy to a martensitic transformation in a predetermined instability temperature interval.

According to another embodiment, the alloy includes titanium at a concentration of from about 48 to about 52 atomic percent, and at least one radiopaque alloying element selected from the group consisting of palladium, platinum and gold, where palladium is at a concentration of from about 15 to about 35 atomic percent, and platinum and gold are at a concentration of from about 10 to about 35 atomic percent. The alloy also includes at least one additional alloying element selected from the group consisting of iron and cobalt at a concentration of from about 0.5 to about 8 atomic percent, and nickel as a balance.

According to another embodiment, the alloy includes titanium at a concentration of from about 48 to about 52 atomic percent, and at least one radiopaque alloying element selected from the group consisting of palladium, platinum and gold, where palladium is at a concentration of from about 15 to about 35 atomic percent, and platinum and gold are at a concentration of from about 10 to about 35 atomic percent. The alloy also includes at least one additional alloying element selected from selected from the group consisting of aluminum, chromium and zirconium, where aluminum and chromium are at a concentration of from over 0 to 2 atomic percent and zirconium is at a concentration of from over 0 to about 6 atomic percent, and the balance of the alloy is nickel.

According to another embodiment, the alloy consists essentially of titanium at a concentration of from about 48 to about 52 atomic percent; at least one radiopaque alloying element selected from the group consisting of palladium, platinum and gold, where palladium is at a concentration of from about 15 to about 35 atomic percent, and platinum and gold are at a concentration of from about 10 to about 35 atomic percent; at least one additional alloying element selected from the group consisting of iron and cobalt at a concentration of from about 0.5 to about 8 atomic percent; at least one further alloying element selected from the group consisting of aluminum, chromium and zirconium, where aluminum and chromium are at a concentration of from over 0 to about 2 atomic percent, and zirconium is at a concentration of from over 0 to about 6 atomic percent; and nickel and inevitable impurities as a balance.

According to another embodiment, the alloy includes at least one radiopaque alloying element at a concentration of from about 10 at. % to about 20 at. %, where the radiopaque alloying element is selected from the group consisting of gold, platinum, and palladium. The nickel-titanium alloy also includes at least one additional alloying element selected from the group consisting of aluminum, chromium, cobalt, iron, and zirconium, where the additional alloying element has a concentration of from about 0.5 at. % to about 4 at. %. The alloy includes titanium at a concentration of from about 48 at. % to about 52 at. % and the balance of the alloy is nickel. Preferably, the alloy has a radiopacity greater than that of a binary nickel-titanium alloy and exhibits a recoverable strain of at least about 2% upon removal of a deforming stress at about body temperature.

According to another embodiment, the alloy includes a radiopaque constituent comprising one or more radiopaque elements selected from the group consisting of gold, platinum, and palladium, where the radiopaque constituent has a concentration of from about 10 at. % to about 35 at. %. The alloy also includes an additional constituent comprising one or more additional alloying elements selected from the group consisting of aluminum, chromium, cobalt, iron, and zirconium, where the additional constituent has a concentration of from about 0.5 at. % to about 13 at. %. The alloy includes titanium at a concentration of from about 48 at. % to about 52 at. %, and the balance of the alloy is nickel. Preferably, the alloy has a radiopacity greater than that of a binary nickel-titanium alloy and exhibits a recoverable strain of at least about 2% upon removal of a deforming stress at about body temperature.

According to one embodiment, the medical device has at least one component comprising a radiopaque alloy having shape memory and superelastic properties, where the radiopaque alloy comprises titanium at a concentration of from about 48 to about 52 atomic percent, at least one element selected from the group consisting of palladium, platinum and gold, where palladium is at a concentration of from about 15 to about 35 atomic percent, and platinum and gold are at a concentration of from about 10 to about 35 atomic percent, and at least one element selected from the group consisting of iron and cobalt at a concentration of from about 0.5 to about 8 atomic percent, with the balance nickel.

According to another embodiment, the medical device has at least one component comprising a radiopaque alloy having shape memory and superelastic properties, where the radiopaque alloy comprises titanium at a concentration of from about 48 to about 52 atomic percent, at least one element selected from the group consisting of palladium, platinum and gold, where palladium is at a concentration of from about 15 to about 35 atomic percent, and platinum and gold are at a concentration of from about 10 to about 35 atomic percent, and at least one element selected from selected from the group consisting of aluminum, chromium and zirconium, where aluminum and chromium are at a concentration of from over 0 to 2 atomic percent and zirconium is at a concentration of from over 0 to about 6 atomic percent, with the balance nickel.

According to another embodiment, the medical device has at least one component comprising a radiopaque alloy having shape memory and superelastic properties, where the radiopaque alloy consists essentially of titanium at a concentration of from about 48 to about 52 atomic percent, at least one element selected from the group consisting of palladium, platinum and gold, where palladium is at a concentration of from about 15 to about 35 atomic percent, and platinum and gold are at a concentration of from about 10 to about 35 atomic percent, at least one element selected from the group consisting of iron and cobalt at a concentration of from about 0.5 to about 8 atomic percent, and at least one element selected from selected from the group consisting of aluminum, chromium and zirconium, where aluminum and chromium are at a concentration of from over 0 to about 2 atomic percent and zirconium is at a concentration of from over 0 to about 6 atomic percent, with nickel and inevitable impurities as the balance. According to another embodiment, the medical device comprises at least one component including a radiopaque nickel-titanium alloy, and the nickel-titanium alloy includes at least one radiopaque alloying element at a concentration of from about 10 at. % to about 20 at. %, where the radiopaque alloying element is selected from the group consisting of gold, platinum, and palladium, and at least one additional alloying element selected from the group consisting of aluminum, chromium, cobalt, iron, and zirconium, where the additional alloying element has a concentration of from about 0.5 at. % to about 4 at. %. The alloy includes titanium at a concentration of from about 48 at. % to about 52 at. %; and the balance is titanium. Preferably, the alloy has a radiopacity greater than that of a binary nickel-titanium alloy and a recoverable strain of at least about 2% upon removal of a deforming stress at about body temperature.

According to another embodiment, the medical device comprises at least one component including a radiopaque nickel-titanium alloy, where the nickel-titanium alloy includes a radiopaque constituent comprising one or more radiopaque elements selected from the group consisting of gold, platinum, and palladium, where the radiopaque constituent has a concentration of from about 10 at. % to about 35 at. %. The alloy also includes an additional constituent comprising one or more additional alloying elements selected from the group consisting of aluminum, chromium, cobalt, iron, and zirconium, where the additional constituent has a concentration of from about 0.5 at. % to about 13 at. %. The alloy includes titanium at a concentration of from about 48 at. % to about 52 at. % and the balance of the alloy is nickel. Preferably, the alloy has a radiopacity greater than that of a binary nickel-titanium alloy and a recoverable strain of at least about 2% upon removal of a deforming stress at about body temperature.

BRIEF DESCRIPTION OF THE DRAWINGS

In order to understand the invention and to see how it may be carried out in practice, preferred embodiments will now be described, by way of non-limiting examples only, with reference to the accompanying drawings, in which.

DETAILED DESCRIPTION OF EXEMPLARY EMBODIMENTS

Figure 1:
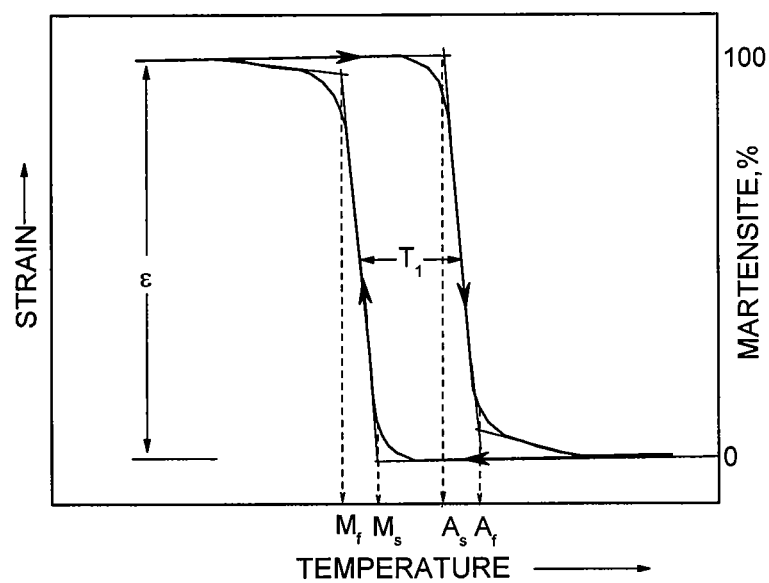
FIG. 1 schematically illustrates a complete thermodynamic cycle of a shape memory alloy in the strain-temperature ($\epsilon$-T) plane.
Figure 2:
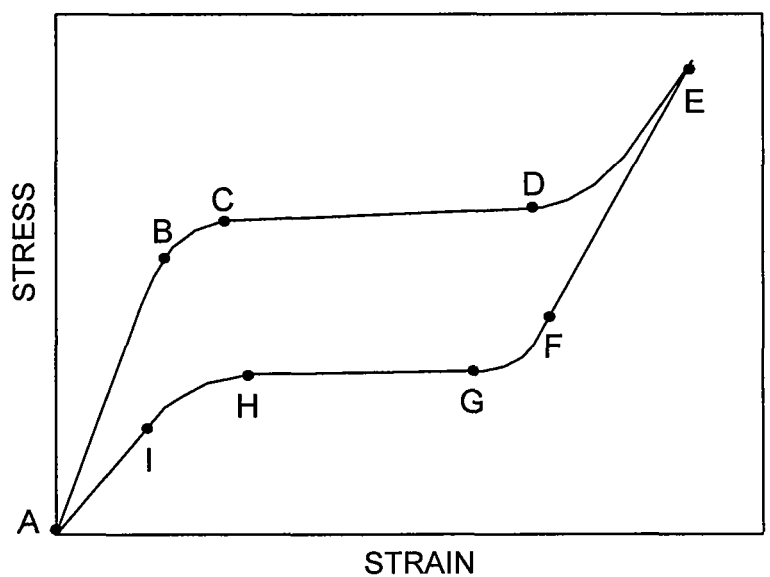
FIG. 2 schematically illustrates a complete thermodynamic cycle of a shape memory alloy in the stress-strain ($\sigma$-$\epsilon$) plane.

The selection of alloying elements for a radiopaque Ti—Ni alloy composition was influenced by the desire to retain the biocompatibility properties of the Ti—Ni alloys, improve the radiopacity of the Ti—Ni alloys, obtain superelastic behavior from the Ti—Ni alloys, and shift the phase transformation temperatures (e.g., $A_f$) to a range appropriate for biomedical use of a device (or article) made of such alloys.

For example, small amounts of Pd and/or Au and/or Pt may not provide the desired level of the radiopacity of the alloy, whereas excessively high concentrations may deteriorate the superelastic properties and undesirably increase the phase transformation temperatures of the alloy. Accordingly, the alloy may include one or more additional alloying elements (e.g., Al, Zr, Cr, Fe, and/or Co) to aid in reducing the phase transformation temperatures to values suitable for an insertable or implantable medical device.

The alloys described herein may be used for the production of medical devices that exhibit both radiopacity and superelastic effects, since the alloys preferably contain at least one radiopaque element and at least one additional alloying element that promotes the retention of superelastic properties in a temperature range suitable for use in the human body.

Thus, according to one embodiment, described herein is a shape memory alloy based on titanium nickelide and having radiopaque and superelastic properties, including: at least one radiopaque element replacing a part of nickel and/or titanium in such amount so as to provide a desired radiopacity of the alloy without causing the destruction of a structure of high-temperature B2-phase; at least one alloying element replacing a part of nickel and/or titanium in such amount so as to maintain the superelasticity properties of the alloy within a desired superelasticity temperature interval; and at least one alloying element replacing a part of nickel and/or titanium in such amount so as to provide instability of the alloy to a martensitic transformation in a predetermined instability temperature interval.

Preferably, each alloying element is an electronic analog of titanium or nickel. Further, the alloying elements may form a continuous series of solid substitution solutions. The influence of the alloying elements on the electronic subsystem of the crystalline lattice of titanium nickelide preferably results in (i) a desired variation of the temperatures of martensitic transformation, and (ii) maximal extension of the temperature interval in which the alloy is unstable to martensitic transformation.

Applicants believe that the radiopacity of the Ti—Ni alloy can be significantly improved and the biocompatibility properties of the material can be retained when palladium (Pd), platinum (Pt) and/or gold (Au) are used as main ternary alloying elements in amounts greater than about 15 atomic percent for Pd, and greater than about 10 atomic percent for Pt and Au. Indeed, as Ni atoms in TiNi are substituted with one or a combination of these elements, secondary phases may not be formed in the quasi-binary section TiNi—TiMe (where, Me is an element selected from Pd, Pt, Au). Without wishing to be bound by theory, Applicants believe that his phenomenon may be explained by the formation of intermetallic compounds having the composition ratio $Ti_{50.0}Me_{50.0}$ (at. %) with B2 superstructure and CsCl type order, i.e., with an atomic structure similar to TiNi, when titanium is alloyed with Pd, Pt, or Au. Therefore, as the Me concentration in $Ti_{50.0}Ni_{50.0-x}Me_x$ alloys is increased along the quasi-binary sections TiNi—TiMe (where Me is selected from Pd, Pt, Au), the structure of the high-temperature B2 phase may be retained. Retaining the B2-phase in all these quasi-binary sections (TiNi—TiPd, TiNi—TiPt, TiNi—TiAu) may make it possible to retain thermoelastic martensitic transformations in $Ti_{50.0}Ni_{50.0-x}Me_x$ alloys and, consequently, to exhibit shape memory and superelasticity effects.

Figure 3A:
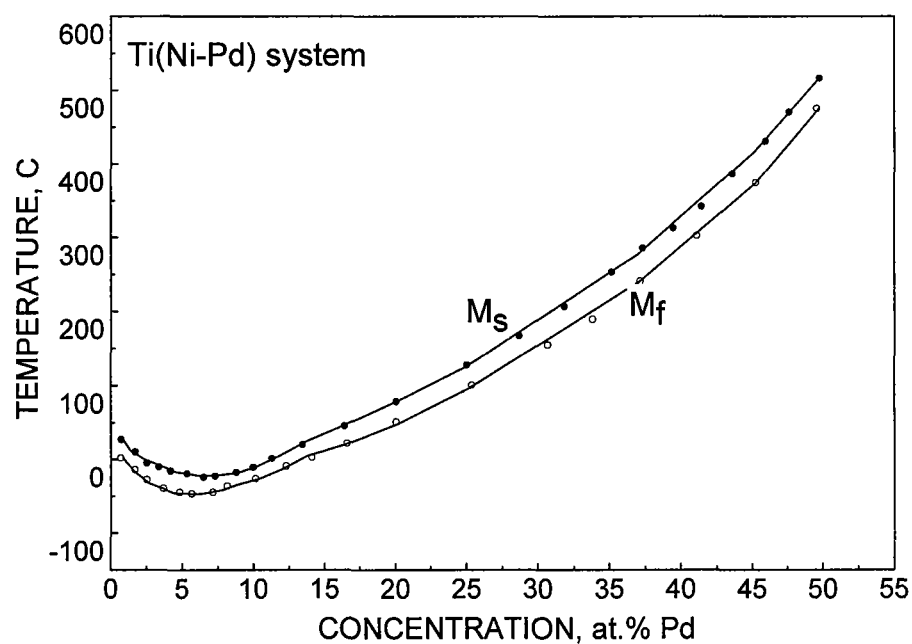
FIGS. 3A-3C are exemplary phase diagrams of martensitic transformations for $Ti_{50.0}Ni_{50.0-x}Pd_x$, $Ti_{50.0}Ni_{50.0-x}Pt_x$ and $Ti_{50.0}Ni_{50.0-x}Au_x$ compositions, respectively.
Figure 3B:
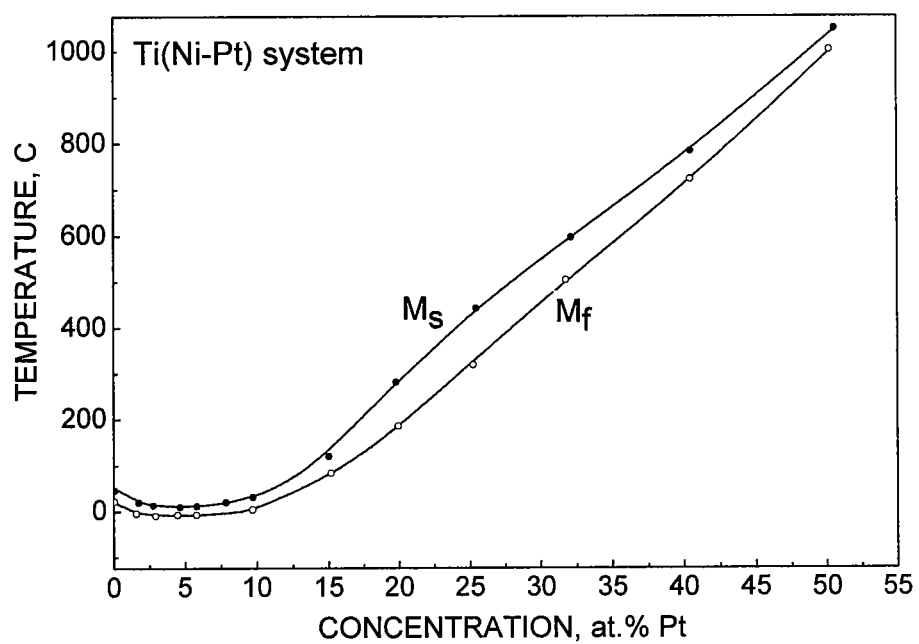
Figure 3C:
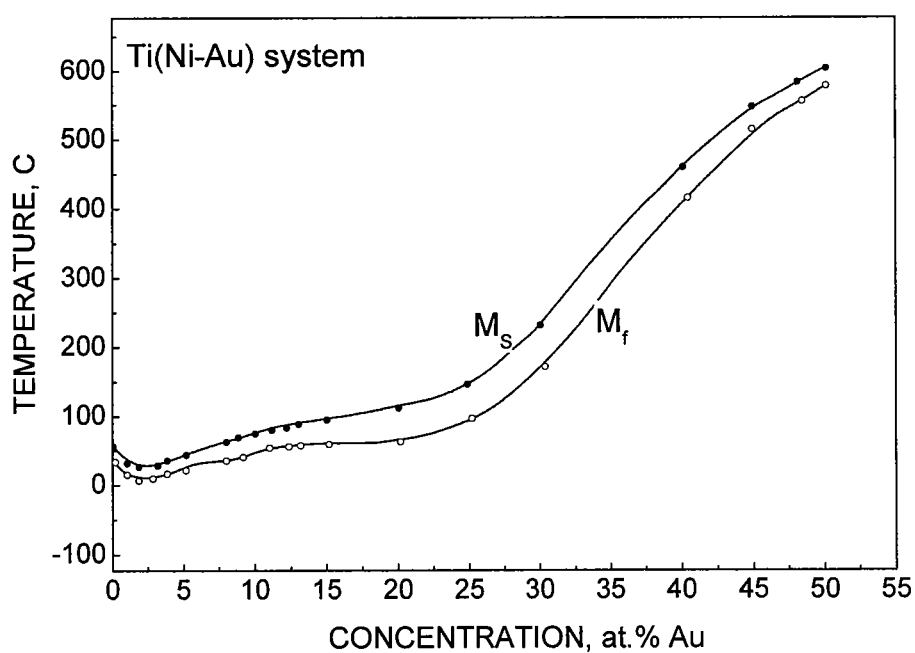

Referring to FIGS. 3A through 3C, exemplary phase diagrams of martensitic transformation temperatures for $Ti_{50.0}Ni_{50.0-x}Pd_x$, $Ti_{50.0}Ni_{50.0-x}Pt_x$ and $Ti_{50.0}Ni_{50.0-x}Au_x$ compositions are shown respectively. As illustrated in FIG. 3A, when when the concentration (x) of Pd increases from 0 to about 7 atomic percent, the martensite start temperature $M_s$ and martensite finish temperature $M_f$ of the $Ti_{50.0}Ni_{50.0-x}Pd_x$ alloy both decrease. The further addition of Pd increases the phase transformation temperatures $M_s$ and $M_f$. Thus, at about 14 atomic percent Pd, the transformation temperatures $M_s$ and $M_f$ correspond to those of binary $Ti_{50.0}Ni_{50.0}$ alloy. The transformation temperatures continue to increase at higher concentrations of Pd.

As illustrated in FIG. 3B, the temperatures of martensitic transformation $M_s$ and $M_f$ slightly decrease when the concentration (x) of Pd increases from 0 to about 3 atomic percent. In the range of about 3 to about 9 atomic percent, the transformation temperatures do not substantially change their values. However, the further addition of Pd beyond about 9 atomic percent results in an increase of $M_s$ and $M_f$.

The phase diagram of martensitic transformation for $Ti_{50.0}Ni_{50.0-x}Au_x$ shows similar behavior (see FIG. 3C). The transformation temperatures $M_s$ and $M_f$ slightly decrease when the concentration (x) of Au increases from 0 to about 3 atomic percent. When x increases beyond this range, the phase transformation temperatures increase, first gradually and then more rapidly beyond a concentration of about 20 at. % Au.

As can be understood from FIGS. 3A through 3C, although the alloying of TiNi with Pd, Pt or Au atoms results in higher radiopacity of the alloy in comparison with binary TiNi, the addition of Pd, Pt or Au at the amounts of greater than about 10 to about 15 atomic percent may increase the phase transformation temperatures of the alloy. An increase in the martensitic transformation temperatures ($M_s$ and $M_f$) upon cooling is generally linked to an increase in the austenitic transformation temperatures ($A_s$ and $A_f$) upon heating.

An increase in the phase transformation temperatures of a shape memory alloy can be in conflict with the intended use of a device made of this alloy. In particular, when the alloy is intended for use in a medical device inserted or implanted within a living body, it may be advantageous for $A_f$ to be less than or equal to the temperature of the living body (e.g., 37° C.). For example, self-expanding stents are generally compressed to a reduced diameter and restrained within a tubular sheath for delivery within a body vessel; once in place at a treatment site, they are deployed superelastically to an expanded configuration so as to contact the vessel wall. During superelastic deployment, stress applied to the stent is released (e.g., the sheath is retracted) so that martensite present in the stent during delivery may transform to austenite and the stent may recover a previous state (e.g., the expanded configuration). If $A_f$ is above body temperature, however, then the stent may not fully deploy automatically upon retraction of the sheath. Accordingly, it is preferably that the Ti—Ni alloy has an austenite finish temperature $A_f$ which is less than or equal to human body temperature so that release of an applied stress is sufficient to trigger the transformation to the austenitic phase. It may also be advantageous for $M_s$ to be less than room temperature (e.g., less than about 20° C.).

Therefore, one or more quaternary alloying elements may be added to the ternary alloy compositions $Ti_{50.0}Ni_{50.0-x}Me_x$ (where Me is selected from Pd, Pt, Au) to reduce the transformation temperatures to the desired temperature range. Preferably, the additional alloying elements do not deteriorate the radiopacity of the alloy. The radiopacity of the alloy aids in positioning the device in the desired location in the body passageway during delivery and deployment. It is also preferred that the quaternary alloying elements do not detrimentally affect the superelastic and/or mechanical properties of the $Ti_{50.0}Ni_{50.0-x}Me_x$ alloy.

According to one embodiment, such a quaternary alloying element can be either iron (Fe) or cobalt (Co). Specifically, it is known that when titanium is alloyed with iron or cobalt at an equiatomic ratio (i.e., $Ti_{50.0}Fe_{50.0}$ and $Ti_{50.0}Co_{50.0}$ (at. %)), intermetallic compounds with the B2 superstructure may be formed, i.e., their structure is similar to that of the high-temperature B2-phase of TiNi. Hence, TiNi alloyed with the atoms of Fe and/or Co instead of Ni may allow the B2-phase structure of the material to be retained.

Figure 4A:
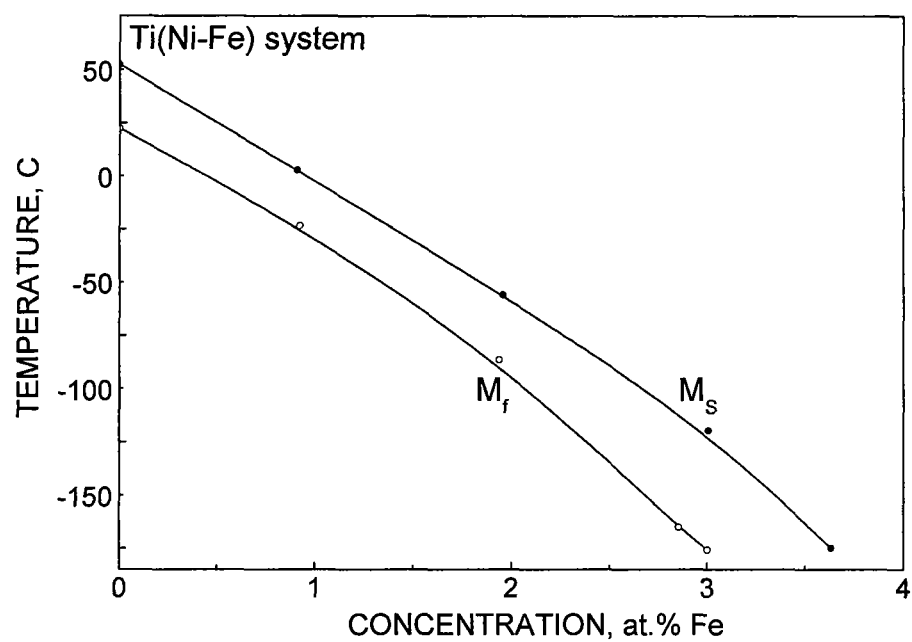
FIGS. 4A and 4B are exemplary phase diagrams of martensitic transformations for $Ti_{50.0}Ni_{50.0-x}Fe_x$, and $Ti_{50.0}Ni_{50.0-x}Co_x$ compositions, respectively.
Figure 4B:
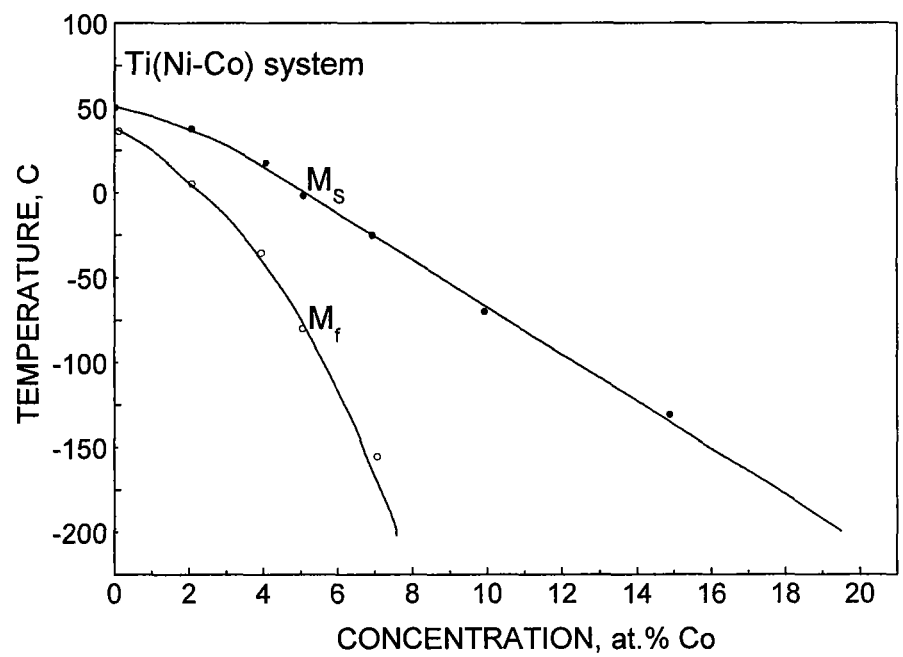

Referring to FIGS. 4A and 4B, exemplary phase diagrams of martensitic transformation for $Ti_{50.0}Ni_{50.0-x}Fe_x$, and $Ti_{50.0}Ni_{50.0-x}Co_x$ compositions are shown, respectively. Alloying of TiNi with atoms of Fe and Co may cause a decrease in the martensitic transformation temperatures. As illustrated in FIG. 4A, the martensite finish temperature $M_f$ of $Ti_{50.0}Ni_{50.0-x}Fe_x$ drastically decreases by about 200° C. when x changes from 0 to about 3 atomic percent. The martensite start temperature $M_s$ of the $Ti_{50.0}Ni_{50.0-x}Fe_x$ alloy behaves in a similar manner at increasing iron concentrations. Likewise, as illustrated in FIG. 4B, the temperature of martensitic transformation $M_f$ of $Ti_{50.0}Ni_{50.0-x}Co_x$ drastically decreases by about 200° C. when x changes from about 0 to 7 atomic percent. The martensite start temperature $M_s$ of the $Ti_{50.0}Ni_{50.0-x}Co_x$ alloy decreases by about 75° C. over the same concentration range.

Moreover, Applicants believe that these alloying elements (Fe and Co, each one separately) may modify the sequence of martensitic transformation from B2→B19' in TiNi to B2→R→B19' in $Ti_{50.0}Ni_{50.0-x}Fe_x$ and/or $Ti_{50.0}Ni_{50.0-x}Co_x$ which may have a favorable effect on the exhibition of the superelasticity effect.

Applicants also believe that when atoms of Ni in TiNi are substituted with both the radiopaque alloying elements Pd, Pt and/or Au together with alloying elements Fe and/or Co, the alloying elements of these two groups independently influence the temperature of martensitic transformation. For example, atoms of Pd introduced instead of atoms of Ni in TiNi may increase the temperature of martensitic transformations in accordance with the diagram of martensitic transformations TiNi—TiPd, while atoms of Fe may decrease the temperature of martensitic transformations in accordance with the diagram of martensitic transformations TiNi—TiFe.

Hence, according to one embodiment of the present invention, the concept of producing a radiopaque NiTi-based alloy exhibiting superelastic behavior around body temperature, i.e., having an austenite finish temperature $A_f$ of less than or equal to 37° C., is as follows.

First, TiNi is preferably alloyed with one or more components selected from Pd, Pt and Au. The one or more components replace a part of nickel and/or titanium and may sufficiently increase the radiopacity without causing the destruction of the superstructure of the high-temperature B2-phase of TiNi. In order to significantly improve the radiopacity of the TiNiMe1 alloy (when Me1 is Pd), it is preferred that the amount of the alloying elements Me1 exceeds 15 atomic percent. Even more preferably, the amount of the alloying element Me1 exceeds 20 atomic percent when Me1 is Pd. Likewise, the radiopacity of the TiNiMe1 alloy (when Me1 is selected from Pt and Au) can sufficiently be improved when the amount of the alloying elements Me1 exceeds 10 atomic percent. Preferably, the amount of the alloying elements Me1 exceeds 15 atomic percent when Me1 is Pt.

Therefore, according to one embodiment of the present invention, the amount of the alloying elements Me1 in the TiNiMe1 alloy is in the range of about 15% to 35% (by atomic percent) when Me1 is Pd, and in the range of about 10% to 35% (by atomic percent) when Me1 is Pt and/or Au.

Preferably, the amount of Ti in the alloy is maintained in the range of about 48% to about 52% (by atomic percent), although other ranges are also possible. If the titanium concentration in the alloy is less than about 48 at. % or more than about 52 at. %), undesirable secondary phases may form. These secondary phases may not undergo martensitic transformations and may have a negative effect on the superelastic behavior of the alloy.

As described above, the adding of the alloying elements Me1 may raise the phase transformation temperatures of the alloy. Therefore, in order to return the phase transformation temperatures to the desired temperature interval (e.g., $A_f$ to less than or equal to human body temperature) without detrimentally affecting the radiopacity, at least one component of Me2 selected from Fe and/or Co can be further added to the alloy by replacing a part of nickel and/or titanium. A preferred amount of Fe and/or Co in TiNiMe1Me2 alloy can be in the range of about 0.5% to about 8% (by atomic percent).

According to another embodiment of the invention, in order to decrease the phase transformation temperatures, one or more components of Me3 selected from aluminum (Al) and chromium (Cr) can be further added to the TiNiMe1Me2 alloy by replacing a part of nickel and/or titanium. Moreover, adding Al and/or Cr may provide a wide temperature interval of instability of the intermetallic compound to the martensitic transformation. For example, adding Al and/or Cr may extend the temperature interval of instability to a range wider than 50 degrees. In this case, the instability temperature interval may be greater than the instability temperature interval of the equiatomic Ti—Ni alloy.

Figure 5A:
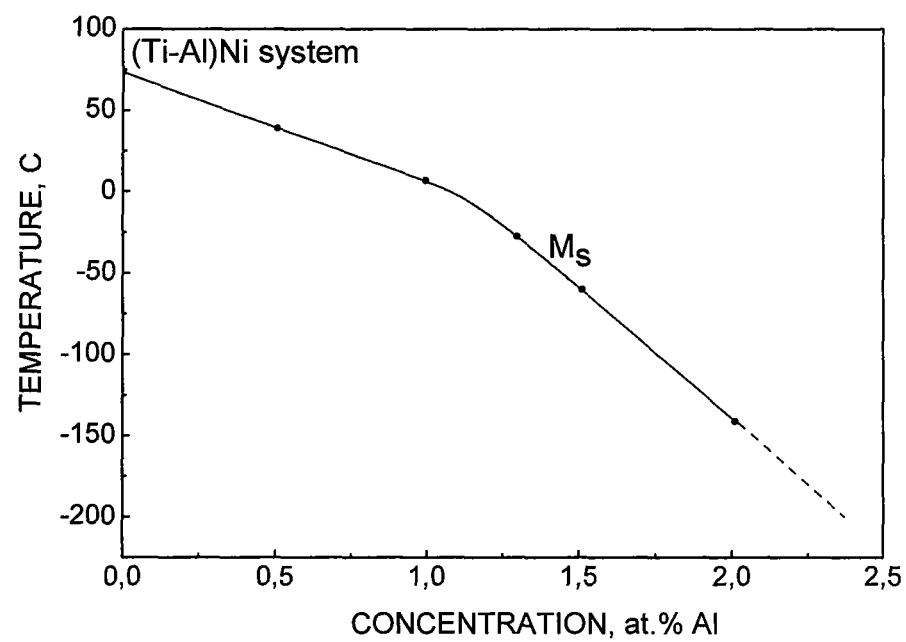
FIG. 5A illustrates an exemplary phase diagram of martensitic transformation for $Ti_{50.0-x}Ni_{50.0}Al_x$ compositions.

FIG. 5A illustrates an exemplary phase diagram of martensitic transformation for $Ti_{50.0-x}Ni_{50.0}Al_x$ compositions. When the concentration (x) of Al in the alloy increases from 0 to about 2 atomic percent, the martensite start temperature $M_s$ decreases.

A preferred amount of Al and/or Cr in the TiNiMe1Me2Me3 alloy is less than about 2 at. %. Applicants believe that when the amount of Al or Cr exceeds 2 at. %, secondary phases may be formed in the alloy that may adversely affect the completeness of the phase transformations and, accordingly, may deteriorate the shape memory and superelastic properties of the material.

According to a further embodiment, zirconium (Zr) can be added either to the TiNiMe1Me2 alloy or to the TiNiMe1Me2Me3 alloy by replacing a part of nickel and/or titanium. Specifically, Zr can be dissolved in the alloy in amounts much greater than Al and Cr. According to one embodiment, Zr can be dissolved in the amount of about 6 at. %, and preferably in the amount of 4 at. %. Preferably, the addition of zirconium does not lead to the formation of a secondary phase (in contrast to the effect expected when atoms of Al and Cr are added). Moreover, adding zirconium may also provide a wide temperature interval of instability of the Ti—Ni alloy to martensitic transformation. The expression "wide temperature range" herein refers to a temperature interval greater than 50 degrees.

Figure 5B:
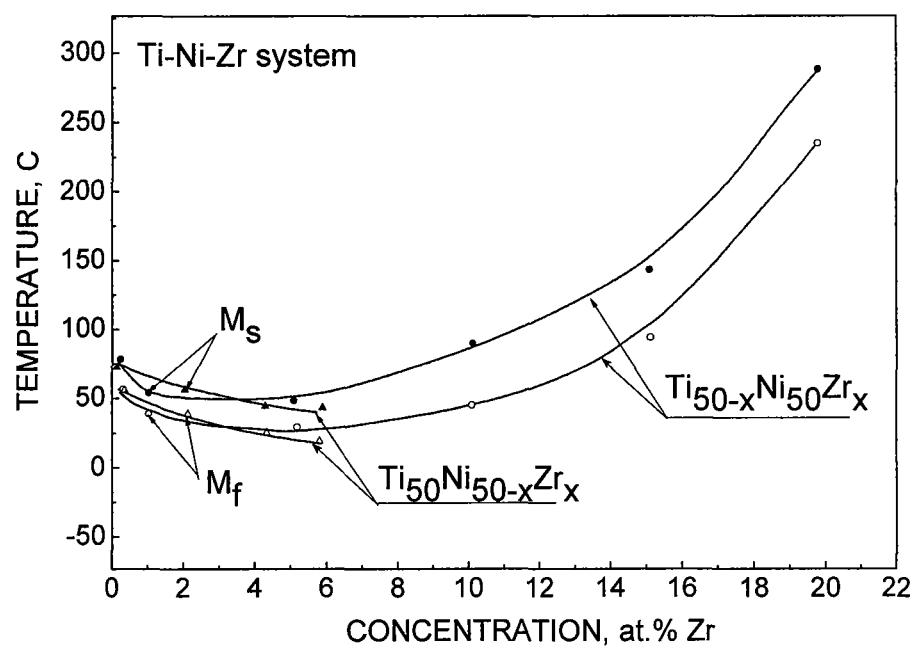
FIG. 5B illustrates an exemplary phase diagram of martensitic transformation for $Ti_{50.0-x}Ni_{50.0}Zr_x$ compositions.

FIG. 5B illustrates exemplary phase diagrams of martensitic transformation for $Ti_{50.0-x}Ni_{50.0}Zr_x$ compositions. When the zirconium concentration (x) increases from 0 to about 4 atomic percent, the martensite start temperature $M_s$ and finish temperature $M_f$ both decrease. The further addition of Zr increases the phase transformation temperatures $M_s$ and $M_f$. At about 9 atomic percent zirconium, the transformation temperatures $M_s$ and $M_f$ correspond to those of binary $Ti_{50.0}Ni_{50.0}$ alloy. Beyond about 9 at. % Zr, the martensitic transformation temperatures further increase.

Figure 6A:
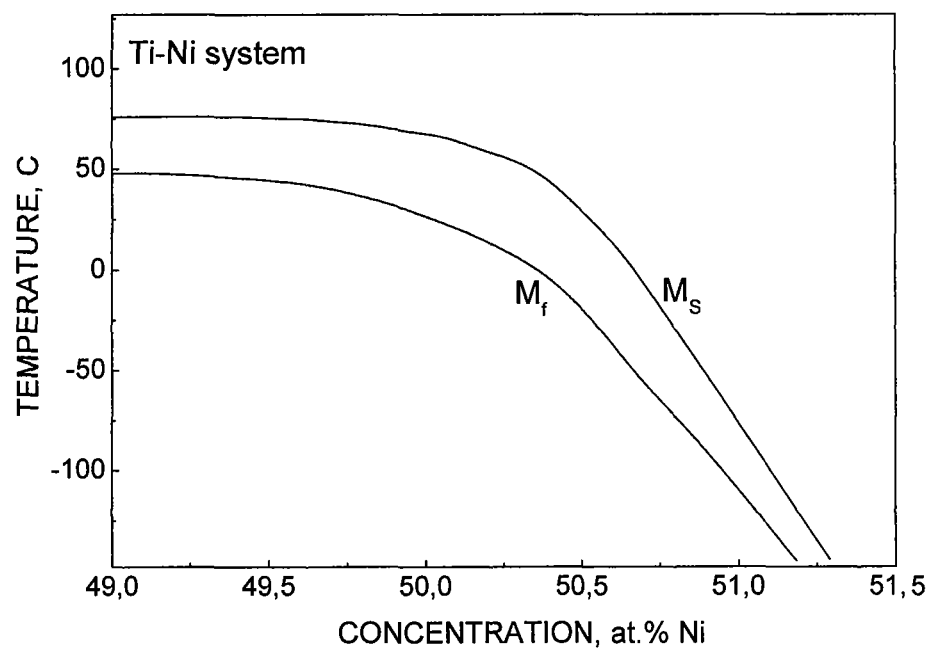
FIGS. 6A and 6B are exemplary phase diagrams of martensitic transformations in alloys $Ti_{50-x}Ni_{50+x}$ subjected to different processing.
Figure 6B:
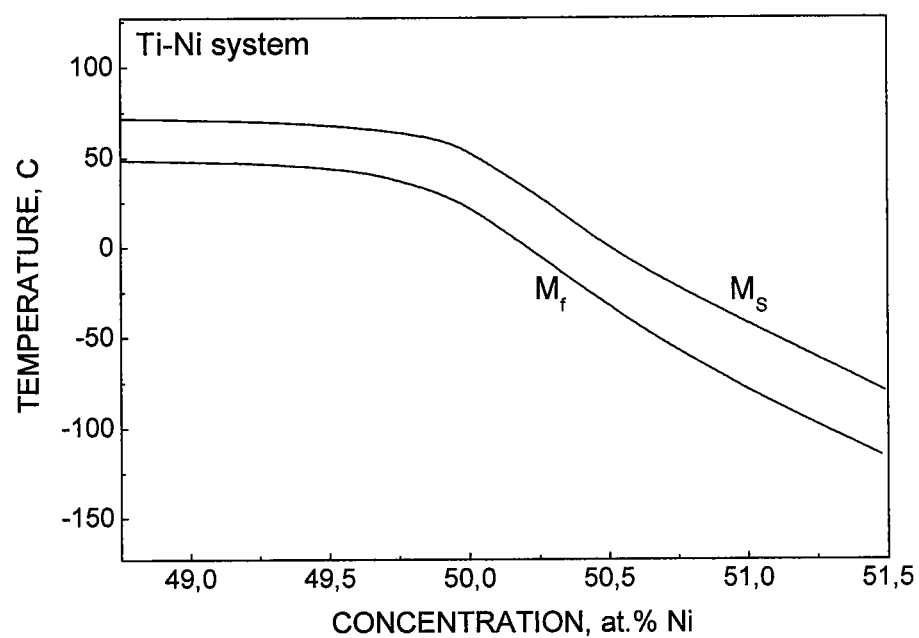

It should also be understood that variation of the phase transformation temperatures can be achieved by departing from the stoichiometric relationship between Ni and Ti in the $Ti_{50.0}Ni_{50.0}$ alloy. FIG. 6A shows an exemplary phase diagram of martensitic transformations in alloys $Ti_{50-x}Ni_{50+x}$, quenched from 1073° K; and FIG. 6B shows an exemplary phase diagram of martensitic transformations in alloys $Ti_{50-x}Ni_{50+x}$ annealed at the temperature of 1073° K (for 1 hour) and then cooled to room temperature. As can be seen, at nickel concentrations higher than about 50.0 at. %, the martensitic transformation temperatures of the TiNi alloy decrease.

Generally speaking, Applicants believe that the upward trend in martensitic transformation temperatures associated with additions of platinum, palladium, or gold at concentrations above about 10 at. % may be balanced by small additions of other alloying elements, such as iron, cobalt, aluminum, and/or zirconium.

Applicants also believe that adding boron (B) to a NiTi-based alloy can improve the ductility of the alloy, where boron plays a role of a plastificator. Thus, according to a further embodiment, boron may be further added to the NiTi-based alloys described herein by replacing a part of nickel and/or titanium. A preferred amount of B in the TiNi-based alloys can be in the range of about 0.05 at. % to about 0.2 at. %.

According to one preferred embodiment, the radiopaque nickel-titanium alloy includes: at least one radiopaque alloying element at a concentration of from about 10 at. % to about 20 at. %, where the radiopaque alloying element is selected from the group consisting of gold, platinum, and palladium; at least one additional alloying element selected from the group consisting of aluminum, chromium, cobalt, iron, and zirconium, where the additional alloying element has a concentration of from about 0.5 at. % to about 4 at. %; titanium at a concentration of from about 48 at. % to about 52 at. %; and nickel as the balance. According to one embodiment, the concentration of the additional alloying element may be in the range of from about 0.5 at. % to about 1.2 at. %. Preferably, the nickel has a concentration of from about 29 at. % to about 52 at. %

For example, the radiopaque nickel-titanium alloy may include gold at a concentration of about 20 at. %, iron at a concentration of about 0.5 at. %, and zirconium at a concentration of about 1 at. %.

In another example, the radiopaque nickel-titanium alloy may include gold at a concentration of about 10 at. %, iron at a concentration of about 1.2 at. %, and zirconium at a concentration of about 1 at. %.

In another example, the radiopaque nickel-titanium alloy may include gold at a concentration of about 15 at. % and aluminum at a concentration of about 1.2 at. %.

In yet another example, the radiopaque nickel-titanium alloy may include gold at a concentration of about 15 at. %, and chromium at a concentration of about 1 at. %.

Alternatively, the radiopaque nickel-titanium alloy may include platinum at a concentration of about 15 at. %, iron at a concentration of about 4 at. %, and zirconium at a concentration of about 1 at. %.

According to another preferred embodiment, the radiopaque nickel-titanium alloy may comprise: a radiopaque constituent comprising one or more radiopaque elements selected from the group consisting of gold, platinum, and palladium, where the radiopaque constituent has a concentration of from about 10 at. % to about 35 at. %; an additional constituent comprising one or more additional alloying elements selected from the group consisting of aluminum, chromium, cobalt, iron, and zirconium, where the additional constituent has a concentration of from about 0.5 at. % to about 13 at. %; titanium at a concentration of from about 48 at. % to about 52 at. %; and the balance nickel, wherein the alloy has a radiopacity greater than that of a binary nickel-titanium alloy and a recoverable strain of at least about 2% upon removal of a deforming stress at about body temperature.

Preferably, the concentration of the radiopaque constituent is from about 10 at. % to about 20 at. % and the concentration of the additional constituent is from about 1 at. % to about 5 at. %. It is also preferred that the nickel has a concentration of from about 29 at. % to about 52 at. %.

For example, the radiopaque constituent may be gold at a concentration of about 20 at. %, and the additional constituent may include iron and zirconium, where the additional constituent has a concentration of about 1.5 at. %.

In another example, the radiopaque constituent may be gold at a concentration of about 10 at. %, and the additional constituent may include iron and zirconium, where the additional constituent has a concentration of about 2.2 at. %.

In another example, the radiopaque constituent may be gold at a concentration of about 15 at. %, and the additional constituent may include one of aluminum and chromium, where the additional constituent has a concentration in the range of from about 1.0 at. % to about 1.2 at. %.

In yet another example, the radiopaque constituent may be platinum at a concentration of about 15 at. %, and the additional constituent may include iron and zirconium, where the additional constituent has a concentration of about 5 at. %.

Phase transformation temperatures (e.g., martensite start temperature $M_s$) of a quaternary or quintary nickel-titanium alloy can be estimated on the basis of the known effect of each individual alloying element on the phase transformation temperatures of the binary TiNi system, assuming that the individual effects are cumulative in a multicomponent system, as described below.

Example 1.1

To broadly estimate the martensite start temperature $M_s$ of a quaternary or quintary Ti—Ni alloy of interest, such as $Ti_{49.5}Ni_{22.2}Au_{25.0}Fe_{2.3}Zr_{1.0}$, a change in the martensite start temperature $M_s$ relative to the binary TiNi system can be derived for each alloying element (e.g., Au, Fe, and Zr) at the appropriate concentration using the data provided in FIGS. 3A to 5B, and then the respective changes may be summed as discussed in this and the related examples below.

For example, the martensite start temperature $M_s$ of the alloy $Ti_{49.5}Ni_{22.2}Au_{25.0}Fe_{2.3}Zr_{1.0}$ can be estimated on the basis of the corresponding temperature increments $\Delta T = \{M_s(Ti_{50.0}Ni_{50.0-x}Me_x) - M_s(Ti_{50.0}Ni_{50.0})\}$ for variations of $T_s$ of ternary compositions of the Ti—Ni alloy alloyed with a ternary element (Me).

In calculations, the value of $M_s(Ti_{50.0}Ni_{50.0}) \approx 55°$ C. for martensite start temperature of $Ti_{50.0}Ni_{50.0}$ was considered. According to the martensitic transformation diagram (shown in FIG. 3C), adding a radiopaque alloying element Au in the amount of 25 at. % by replacing 25 at. % of Ni increases $M_s$ from about 55° C. for the binary TiNi alloy to about 140° C. for the $Ti_{50}Ni_{25}Au_{25}$ alloy. Accordingly, $\Delta T_{Au} \approx \{M_s(Ti_{50}Ni_{25}Au_{25}) - M_s(TiNi)\} \approx (140°$ C.$-60°$ C.$) \approx 80°$ C.

Further, in order to decrease $M_s$, the alloying element Fe can be added. According to the martensitic transformation diagram shown in FIG. 4A, adding the alloying element Fe in the amount of 2.3 at. % by replacing 2.3 at. % Ni decreases $M_s$ from about +55° C. for the binary TiNi alloy to about −75° C. for the $Ti_{50}Ni_{47.7}Fe_{2.3}$ alloy. Accordingly, $\Delta T_{Fe} \approx \{M_s(Ti_{50}Ni_{47.7}Fe_{2.3}) - M_s(TiNi)\} \approx (-75°$ C.$-55°$ C.$) \approx -130°$ C.

Applicants believe that adding Fe in the amount of 2.3 at. % to $Ti_{50}Ni_{25}Au_{25}$ by replacing 2.3 at. % of Ni can decrease $M_s$ of the $Ti_{50}Ni_{25}Au_{25}$ alloy by about the same value $\Delta T_{Fe} \approx -130°$ C. Thus, the value of $M_s(Ti_{50}Ni_{22.7}Au_{25.0}Fe_{2.3})$ may be estimated to be approximately equal to $\{M_s(Ti_{50}Ni_{25}Au_{25}) + \Delta T_{Fe}\} \approx (140°$ C.$-130°$ C.$\approx 10°$ C.). One can also calculate a value $\Delta T_{Au}+\Delta T_{Fe} \approx 80°$ C.+(−130° C.)=−50° C. which represents the estimated combined effect of 25 at. % Au and 2.3 at. % Fe on the binary TiNi system. Accordingly, $M_s(Ti_{50}Ni_{22.7}Au_{25.0}Fe_{2.3}) \approx M_s(TiNi)+\Delta T_{Au}+\Delta T_{Fe} \approx 55°$ C.+ (−50° C.)≈+5° C. Taking into account the hysteresis of the phase transformation temperatures (see FIG. 1) and assuming a temperature differential $T_1$ of approximately 30° C. to 35° C., $A_f$ may be estimated to be ≈35° C.-40° C.

Finally, the transformation temperatures can be further reduced by adding the alloying element Zr in the amount of 1.0 at. % by replacing 0.5 at. % of Ti and 0.5 at. % of Ni. According to the martensitic transformation diagram shown in FIG. 5B, adding the alloying element Zr in the amount of 1.0 at. % by replacing 0.5 at. % of Ti and 0.5 at. % Ni decreases $M_s$ to the temperature $M_s(Ti_{49.5}Ni_{49.5}Zr_{1.0}) \approx 45°$ C. from an assumed binary value of 55° C. Accordingly, $\Delta T_{Zr} \approx \{M_s(Ti_{49.5}Ni_{49.5}Zr_{1.0})-M_s(TiNi)\} \approx (45°$ C.-55° C.)≈−10° C.

Hence, the temperature $M_s$ of the multi-component $Ti_{49.5}Ni_{22.2}Au_{25.0}Fe_{2.3}Zr_{1.0}$ alloy can be estimated as $M_s \approx \{M_s(TiNi)+\Delta T_{Au}+\Delta T_{Fe}+\Delta T_{Zr}\} \approx \{55°$ C.+80° C.+(−130° C.)+(−10° C.)}≈−5° C., where $M_s$ of TiNi is assumed to be 60° C. Taking into account the hysteresis of the phase transformation temperatures as above, the temperature of the onset of the reverse martensitic transformation in such an alloy can be estimated as $A_f$=20° C.-30° C.

A concentration C of the balance element (e.g., Ni) in atomic percent is determined from the formula $C_{Ni}$=(100-$C_{Ti}$—$C_{Au}$—$C_{Fe}$—$C_{Zr}$) at. %.

Example 1.2

The same procedure as described in Example 1.1 may be employed to estimate the transformation temperatures for a $Ti_{48.7}Ni_{35.0}Au_{15.0}Al_{1.3}$ alloy.

Referring to FIG. 3C, alloying a binary TiNi alloy with a radiopaque alloying element Au in the amount of 15 at. % by replacing 15 at. % of nickel increases $M_s$ from about 55° C. for the binary TiNi system to approximately 100° C. for the $Ti_{50}Ni_{35}Au_{15}$ alloy. Thus, $M_s(Ti_{50}Ni_{35}Au_{15}) \approx 100°$ C. and $\Delta T_{Au} \approx (100°$ C.-55° C.)=45° C.

Further, in order to decrease $M_s$ and facilitate superelastic properties, for example, such an alloying element as Al can be used. Referring to the martensitic transformation diagram for $Ti_{50.0-x}Ni_{50.0}Al_x$ of FIG. 5A, adding Al in the amount of 1.3 at. % by replacing 1.3 at. % of Ti decreases $M_s$ from about 74° C. to approximately −37° C. for the $Ti_{48.7}Ni_{50.0}Al_{1.3}$ alloy. Thus, $M_s(Ti_{48.7}Ni_{50.0}Al_{1.3}) \approx -37°$ C. and $\Delta T_{Al} \approx (-37°$ C.-74° C.)≈−111° C.

Hence, the temperature $M_s$ of the multi-component $Ti_{48.7}Ni_{35.0}Au_{15.0}Al_{1.3}$ alloy alloy can be estimated as $M_s \approx \{M_s(TiNi)+\Delta T_{Au}+\Delta T_{Al}\} \approx \{55°$ C.+45° C.+(−111° C.)}≈−11° C., where $M_s$ of TiNi is assumed to be 55° C. Taking into account the hysteresis of the phase transformation temperatures as above, the temperature of the onset of the reverse martensitic transformation in such an alloy can be estimated as $A_f$=19° C.-24° C.

Example 1.3

The same procedure as described in Example 1.2 may be employed to estimate the transformation temperatures for a $Ti_{48.7}Ni_{35.0}Au_{15.0}Cr_{1.0}$ alloy.

In order to fabricate a multi-component alloy based on titanium nickelide and having desired radiopaque property and desired martensitic transformation temperature, first, a binary TiNi alloy can be alloyed similar to Example 2 with a radiopaque alloying element Au in the amount of 15 at. % by replacing 15 at. % of nickel. As described in the previous example, this alloying increases $M_s$ from about 55° C. to the temperature $M_s(Ti_{50}Ni_{35}Au_{15}) \approx 100°$ C. (i.e., by $\Delta T_{Au} \approx 45°$ C.).

According to this example, in order to decrease $M_s$, an alloying element such as Cr can be used. For instance, it is known that adding Cr in the amount of 1.0 at. % by replacing 1.0 at. % of Ni decreases $M_s$ to the temperature $M_s(Ti_{50.0}Ni_{49.0.0}Cr_{1.0}) \approx -80°$ C. (i.e., by $\Delta T_{Cr} \approx -135°$ C., assuming that the $M_s$ of TiNi is 55° C.). Further assuming that adding Cr in the amount of 1.0 at. % to a ternary alloy $Ti_{50.0}Ni_{35.0}Au_{15.0}$ by replacing 1.0 at. % of Ni will decrease $M_s$ by about the same value ($\Delta T_{Cr} \approx -135°$ C.) as in the case of addition to the binary alloy $Ti_{50}Ni_{50}$, then the temperature $M_s(Ti_{50.0}Ni_{34.0}Au_{15.0}Cr_{1.0})$ can be estimated to be about −35° C. Accordingly, the temperature of the onset of the reverse martensitic transformation for $Ti_{48.7}Ni_{35.0}Au_{15.0}Cr_{1.0}$ can approximately be estimated as $A_f$=−5° C. to 0° C.

TABLE 1

Preferred Composition Ranges for the Ti—Ni Alloys

| Type | Chemical formula |
|---|---|
| General example | $Ti_{48-52}Ni_{balance}Au_{10-35}Fe_{0.5-8.0}Zr_{0.1-4.0}$ |
| Preferred example | $Ti_{48-52}Ni_{balance}Au_{10-25}Fe_{0.5-4.0}Zr_{0.1-2.0}$ |
| Most preferred example | $Ti_{48-52}Ni_{balance}Au_{10-20}Fe_{0.5-2.0}Zr_{0.1-1.0}$ |
| General example | $Ti_{48-52}Ni_{balance}Au_{10-35}Co_{0.5-8.0}Zr_{0.1-4.0}$ |
| Preferred example | $Ti_{48-52}Ni_{balance}Au_{10-25}Co_{0.5-6.0}Zr_{0.1-2.0}$ |
| Most preferred example | $Ti_{48-52}Ni_{balance}Au_{10-20}Co_{0.5-4.0}Zr_{0.1-1.0}$ |
| General example | $Ti_{48-52}Ni_{balance}Pt_{10-35}Fe_{0.5-8.0}Zr_{0.1-4.0}$ |
| Preferred example | $Ti_{48-52}Ni_{balance}Pt_{10-25}Fe_{0.5-6.0}Zr_{0.1-2.0}$ |
| Most preferred example | $Ti_{48-52}Ni_{balance}Pt_{10-20}Fe_{0.5-4.0}Zr_{0.1-1.0}$ |
| General example | $Ti_{48-52}Ni_{balance}Pd_{15-35}Fe_{0.5-5.0}Zr_{0.1-4.0}$ |
| Preferred example | $Ti_{48-52}Ni_{balance}Pd_{15-25}Fe_{0.5-3.0}Zr_{0.1-2.0}$ |
| Most preferred example | $Ti_{48-52}Ni_{balance}Pd_{15-20}Fe_{0.5-2.0}Zr_{0.1-1.0}$ |
| General example | $Ti_{48-52}Ni_{balance}Au_{10-35}$(Al or Cr replacing Ti or Ni)$_{0.5-2.5}$ |
| Preferred example | $Ti_{48-52}Ni_{balance}Au_{10-25}$(Al or Cr replacing Ti or Ni)$_{0.5-1.8}$ |
| Most preferred example | $Ti_{48-52}Ni_{balance}Au_{10-20}$(Al or Cr replacing Ti or Ni)$_{0.5-1.5}$ |
| General example | $Ti_{48-52}Ni_{balance}Pd_{15-35}Cr_{0.5-2.0}Zr_{0.0-1.0}$ |
| Preferred example | $Ti_{48-52}Ni_{balance}Pd_{15-25}Cr_{0.5-1.5}Zr_{0.0-1.0}$ |
| Most preferred example | $Ti_{48-52}Ni_{balance}Pd_{15-20}Fe_{0.5-1.2}Zr_{0.0-1.0}$ |
| General example | $Ti_{48-52}Ni_{balance}Pt_{10-15}Cr_{0.5-2.0}Zr_{0.0-1.0}$ |

Suitable composition ranges for the radiopaque nickel-titanium alloy are presented in Table 1. The alloys described hereinabove can be fabricated by melting Ti, Ni mixed with alloying elements according to the compositions suggested above. According to one embodiment, the melting of the composition can be carried out by mixing all the alloying elements together and then applying elevated temperatures to the mixture. According to another embodiment, the melting of the composition can be carried out by first mixing and melting only base alloying elements with a consequent cooling of this mixture, and then adding one or more secondary alloying elements and remelting the mixture one or more times again.

The mixture can, for example, be heated and molten in an induction furnace, arc furnace or other suitable oven in a protective atmosphere. The mixture may be molten in a purified helium or argon atmosphere. For instance, the melting can be carried out at a constant temperature, e.g. at a temperature within the temperature interval of about 1200° C. to 1400° C. Alternatively, the melting can be carried out by elevating the temperature at a rate of, for example, 5° C. per minute to 50° C. per minute from about room temperature to a temperature in the range of about 1200° C. to 1400° C. Thereafter, the melt can be poured to a cooled mold, e.g. to a water-cooled mold made of brass, copper or other suitable material. When desired, the ingot can then be remelted for consistency. After cooling, the solidified body (ingot) can be taken from the mold and hot-worked into a bar, a wire or a slab. After melting and cooling, the ingot can be annealed by, for example, keeping the ingot at a temperature in the range of from about 800° C. to 1100° C. for a time period between 10 minutes and 2 hours.

Embodiments of the fabrication method described above were employed to produce 29 alloy compositions in the form of ingots or buttons. Three of the 29 alloys were binary Ti—Ni compositions. Seven of the 29 alloys included one additional alloying element (Pd, Pt, Au, or Cu) beyond titanium and nickel. Nine of the 29 alloys included two additional alloying elements (Au+Al or Au+Cr). Ten of the 29 alloys included three additional alloying elements (Pt+Fe+Zr or Au+Fe+Zr).

Referring to Table 2, alloys designated as numbers 4, 13, 14, 15, and 16 were selected from all of the melted compositions for further investigation. Alloys designated as numbers 4/2, 4/3, and 15/2 are remelts of alloys 14 and 15, respectively. As will be discussed below, substantial recoverable strains were obtained from stress-strain tests of each of these alloys. Preferably, the alloy has a recoverable strain of at least about 2% upon removal of a deforming stress at about body temperature. It is preferred that the recoverable strain is at least about 5%. It is believed that the selected alloys may have sufficient ductility to undergo further mechanical working into forms such as strip, wire or plate.

Bars of specified dimensions were prepared from samples 4, 13, 14, and 16 by an electroerosion cutting technique for the purpose of conducting mechanical tests on the specimens. Specifically, for measurements of stress versus strain (i.e., to obtain $\sigma(\epsilon)$ curves), bars having a rectangular cross-section of 1.2 mm by 1.2 mm and a length of 26.0 mm were fabricated from the ingots. The sides of the bars were polished, and the bar samples were tested using a machine equipped with a thermal chamber in order to evaluate the superelastic behavior of the specimens at different temperatures. The mechanical tests were carried out by applying torsional stresses to the samples.

Specifically, an installation of a contrary tensional pendulum was utilized to perform the tests. Each sample was placed vertically in the installation. The bottom end of the sample was clamped by a split terminal and fixed. The top end of the sample was also clamped by the split terminal, and to this end a gradually increasing external tension in the form of a torsional stress was applied. Thus, a torsional strain of, for example, up to about $\gamma=5\%$ was applied to the sample. The installation was placed in a heating furnace for tests at temperatures ranging from room temperature (about 20° C.) up to 200° C., and the installation was placed into a cooling device for tests conducted at temperatures in the range of from about room temperature to about −196° C.

It should be noted that thermal treatments (annealing, aging, etc.) of the alloys at different temperatures and/or mechanical treatments (drawing, swaging, etc.) may provide a means of varying the phase transformation temperatures of the alloys. This phenomenon can be associated with the formation of secondary phases and precipitates (distinguished from the B2 phase) during thermal processing. Annealing and/or aging may provide dilution or precipitation of secondary phases. In the presence of secondary phases, the composition of the parent phase may be altered, and thus the phase transformation temperatures of the alloy may be changed. Thus, correction of the phase transformation temperatures may be effected by a further thermal treatment of the alloy. In some cases, the specimens were tested in the as-cast state and/or following one or more annealing treatments. High temperature anneals of the specimens were conducted in a vacuum environment.

TABLE 2

Melted Alloy Compositions in Atomic Percent (at. %)

| Note | # | Base | | Additional | | | | | | |
|---|---|---|---|---|---|---|---|---|---|---|
| | | Ti | Ni | Pd, Cu | Pt | Au | Fe | Al | Cr | Zr |
| Etalon composition | 0-1 | 50.0 | 50.0 | | | | | | | |
| Etalon composition | 0-2 | 49.5 | 50.5 | | | | | | | |
| Etalon composition | 0-3 | 49.0 | 51.0 | | | | | | | |
| Etalon composition | 0-4 | 50.0 | 42.5 | 7.5-Pd | | | | | | |
| Re-melted six times | 1 | 50.0 | 26.0 | | 20.0 | | 3.0 | | | 1.0 |
| Re-melted six times | 2 | 49.2 | 10.6 | | 35.0 | | 4.2 | | | 1.0 |
| Re-melted six times | 3 | 49.5 | 23.3 | | 25.0 | | 1.2 | | | 1.0 |
| Re-melted six times | 4 | 49.5 | 29.0 | | 20.0 | | 0.5 | | | 1.0 |
| Re-melted six times | 5 | 50.0 | 33.0 | | 15.0 | | 1.0 | | | 1.0 |
| Re-melted six times | 6 | 48.8 | 35.0 | | | 15.0 | | 1.2 | | |
| Re-melted six times | 7 | 48.5 | 35.0 | | | 15.0 | | 1.5 | | |
| Re-melted six times | 8 | 48.2 | 35.0 | | | 15.0 | | 1.8 | | |
| Re-melted six times | 9 | 49.0 | 35.0 | | | 15.0 | | | 1.0 | |
| Re-melted six times | 10 | 48.75 | 35.0 | | | 15.0 | | | 1.25 | |
| Re-melted six times | 11 | 48.5 | 35.0 | | | 15.0 | | | 1.5 | |
| Etalon for samples # 6-11 | 12 | 50.0 | 35.0 | | | 15.0 | | | | |
| Alloy #4 re-melted nine times | 4/2 | 49.5 | 29.0 | | | 20.0 | 0.5 | | | 1.0 |
| Ti, Ni, Fe, Zr melted and re-melted 3 times; Au added and alloy re-melted 6 times | 4/3 | 49.5 | 29.0 | | | 20.0 | 0.5 | | | 1.0 |
| Re-melted six times | 13 | 50.0 | 30.0 | | 15.0 | | 4.0 | | | 1.0 |
| Re-melted six times | 14 | 50.0 | 37.8 | | | 10.0 | 1.2 | | | 1.0 |
| Re-melted six times | 15/1 | 49.3 | 34.5 | | | 15.0 | 1.2 | | | |

TABLE 2-continued

Melted Alloy Compositions in Atomic Percent (at. %)

| | | Base | | Additional | | | | | | |
|---|---|---|---|---|---|---|---|---|---|---|
| Note | # | Ti | Ni | Pd, Cu | Pt | Au | Fe | Al | Cr | Zr |
| Ti, Ni, Au melted and re-melted 3 times; Al added and alloy re-melted 6 times | 15/2 | 49.3 | 34.5 | | | 15.0 | | 1.2 | | |
| Re-melted six times | 16 | 50.2 | 33.8 | | | 15.0 | | | 1.0 | |
| Re-melted six times | 17 | 50.0 | 17.0 | | 20.0 | | 12.0 | | | 1.0 |
| Re-melted six times | 1-Kh | 49.0 | 41.0 | | | 10.0 | | | | |
| Re-melted six times | 2-Kh | 49.0 | 36.0 | | | 15.0 | | | | |
| Re-melted six times | 3-Kh | 49.0 | 31.0 | | | 20.0 | | | | |
| Re-melted six times | 4-Kh | 49.0 | 36.0 | | 15.0 | | | | | |
| Re-melted six times | 5-Kh | 49.0 | 39.0 | 12-Cu | | | | | | |

The fabrication method described above can be better understood from the following specific non-limiting examples of the experimental characteristics of several alloys from Table 2 which are intended to illustrate the present invention and to teach a person of the art how to make and use the invention. These examples are not intended to limit the scope of the invention or its protection in any way.

Example 2.1

According to this example, the specimen designated as alloy #4 in Table 2 was fabricated as follows. A mixture was prepared from the following elements of the indicated purities: titanium, 99.9%; nickel, 99.99%; gold, 99.95%; iron, 99.95%; and zirconium, 99.99%. The mixture weight was 50 g, and it contained 14.578 grams of titanium, 10.468 grams of nickel, 24.221 grams of gold, 0.1717 gram of iron and 0.5609 gram of zirconium which corresponds to the composition: 49.5 at. % Ti; 29.0 at. % Ni; 20.0 at. % Au; 0.5 at. % Fe; and 1.0 at. % Zr ($Ti_{49.5}Ni_{29.0}Au_{20.0}Fe_{0.5}Zr_{1.0}$). The mixture was molten in an arc furnace in a purified argon atmosphere (about 0.4 atm Ar) at a temperature of about 1300° C. in a water-cooled copper mold. The arc current was 500 A. Once all the components were melted, the arc was maintained for one additional minute, and then the arc was switched off. The melt was then cooled to a temperature of about 40° C. To improve the homogeneity of the alloy, the ingot was remelted six times. After cooling between each remelt, the ingot was turned upside down. After the final cooling, bars having a rectangular cross-section of 1.2 mm by 1.2 mm and a length of 26.0 mm were fabricated and tested as described above to evaluate the superelastic behavior of the specimen.

Figure 9:
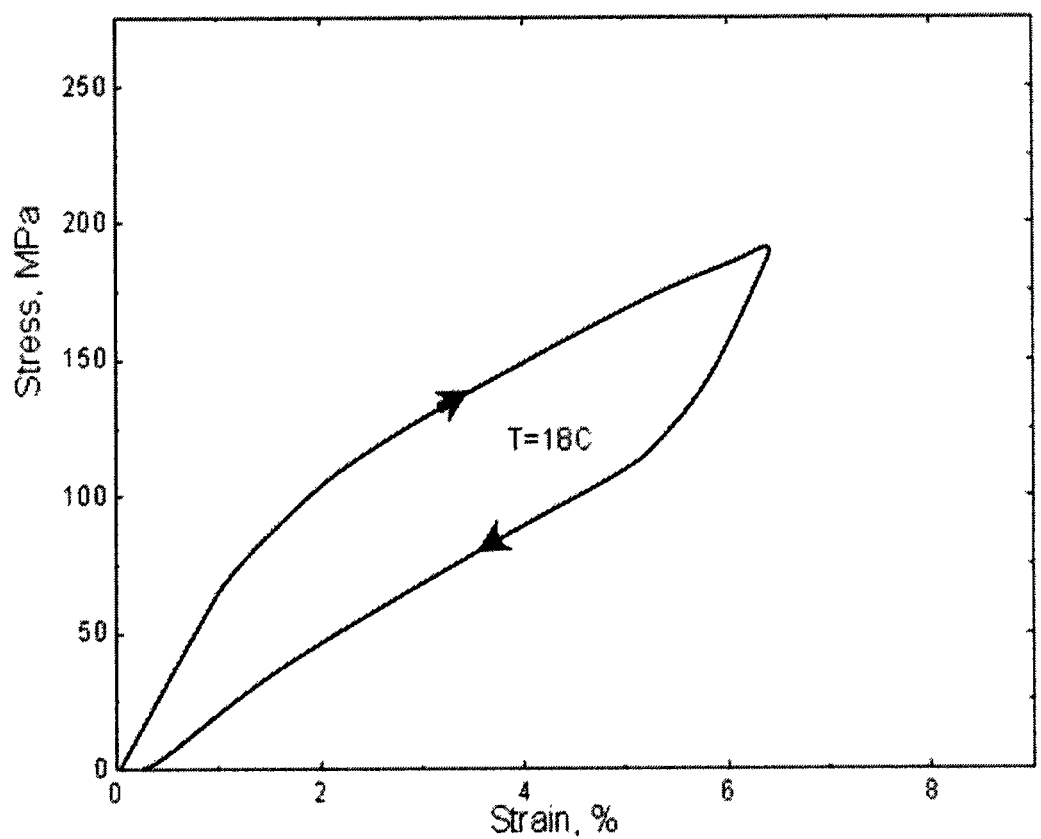
FIGS. 9-14 illustrate stress-strain plots for measurements at various temperatures of exemplary alloys prepared in accordance with the present disclosure.

FIG. 9 illustrates a stress-strain plot for measurements at the temperature of 18° C. of a $Ti_{49.5}Ni_{29.0}Au_{20.0}Fe_{0.5}Zr_{1.0}$ sample prepared as described above. The sample was heated at the temperature of 320° C. over 30 minutes before the mechanical test. The plot shows a stress-strain hysteresis which is characteristic of superelastic behavior. As is apparent from the plot, the $Ti_{49.5}Ni_{29.0}Au_{20.0}Fe_{0.5}Zr_{1.0}$ alloy achieves a recoverable strain of 6.1% in response to the applied torsional stress of 195 MPa at a test temperature of 18° C.

Figure 10:
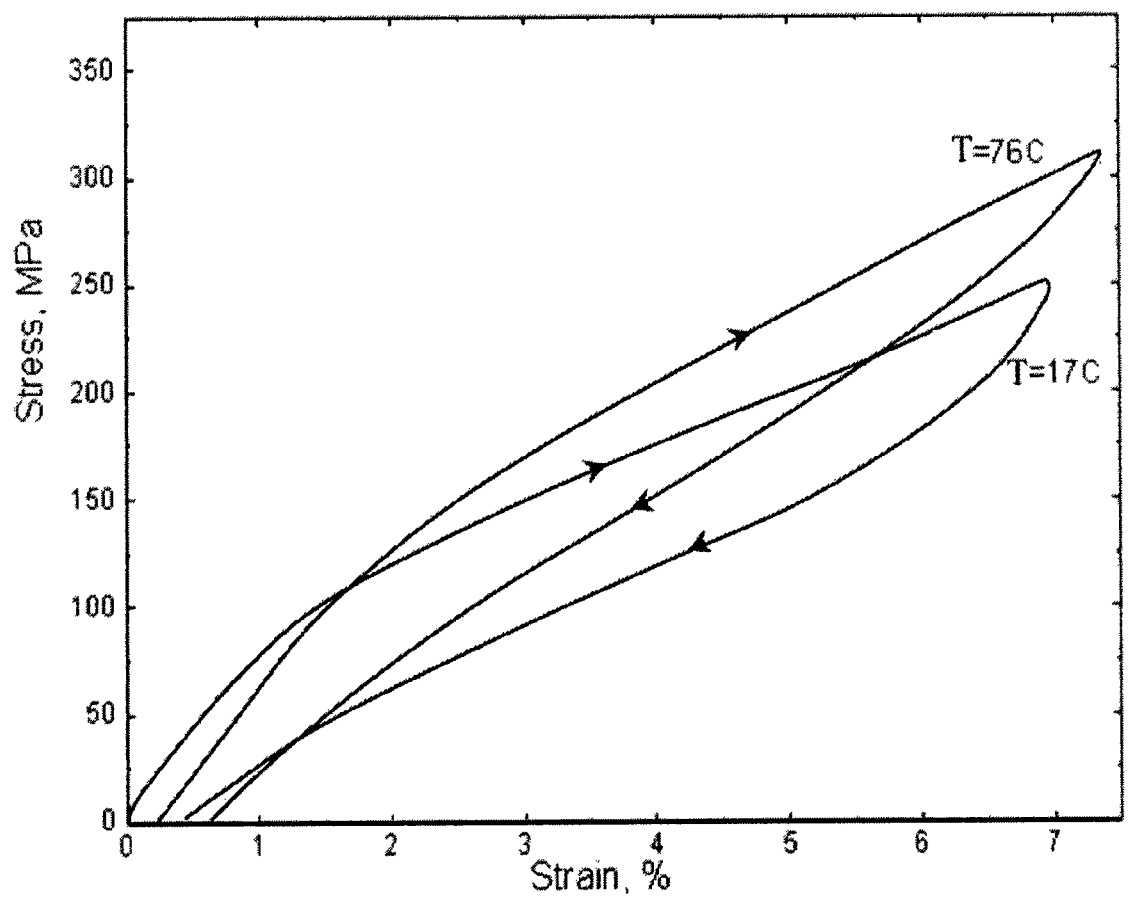

Referring to FIG. 10, stress-strain plots are illustrated for measurements at the temperatures of 17° C. and 76° C. of the $Ti_{49.5}Ni_{29.0}Au_{20.0}Fe_{0.5}Zr_{1.0}$ sample prepared as described above, and then annealed at the temperature of 800° C. for over 120 minutes. Similar to the previous case, the sample was heated at the temperature of 320° C. over 30 minutes before the mechanical test. As in FIG. 9, the plot shows a stress-strain hysteresis which is characteristic of superelastic behavior. The $Ti_{49.5}Ni_{29.0}Au_{20.0}Fe_{0.5}Zr_{1.0}$ alloy exhibits a recoverable strain of about 6.5% under a torsional stress of 255 MPa at 17° C. At 76° C., the alloy exhibits a recoverable strain of about 6.7% at a torsional stress of 315 MPa.

Table 3 below provides a summary of the recoverable strain values obtained for sample #4 from the stress-strain tests. Depending on the test temperature, heat treatment, and the maximum applied torsional stress ($\tau_{max}$), recoverable strain values ($\gamma_{resilience}$) in the range of from 3.9% to 7.1% were obtained. Also given in the table is the residual plastic component of the deformation, $\gamma_{residual}$.

It is postulated, based on these data, that a superelastic $Ti_{49.5}Ni_{29.0}Au_{20.0}Fe_{0.5}Zr_{1.0}$ alloy having an austenite finish temperature $A_f$ of less than about 17° C. may be fabricated as described herein. Accordingly, it is concluded that superelastic behavior may be obtained at human body temperature (37° C.) from a quintary nickel-titanium alloy including Au, Fe, and Zr and having the composition of alloy #4.

TABLE 3

Recoverable Strain Data for Alloy #4.

| Heat Treatment | $T_{experiment}$, ° C. | $\tau_{maximum}$, MPa | $\gamma_{resilience}$, % | $\gamma_{residual}$, % |
|---|---|---|---|---|
| 320° C., 30 min. | 18 | 195 | 6.1 | 0.3 |
| | | 250 | 7.1 | 0.4 |
| | 60 | 255 | 5.8 | 0.1 |
| | 116 | 330 | 5.6 | 0.7* |
| | −24 | 170 | 3.9 | 1.0** |
| 800° C., 1 hour, Slow cooling with furnace | 17 | 255 | 6.5 | 0.5 |
| | 76 | 315 | 6.7 | 0.25 |
| | 122 | 334 | 5.5 | 0.2 |

*At a subsequent heating to a temperature higher than that of the experiment, an additional 0.4% strain recovery is observed. The residual plastic component of the deformation $\gamma_{residual}$ is 0.3% in this case.
**At a subsequent heating to a temperature higher than that of the experiment, full recovery is obtained.

Example 2.2

The alloy designated in Table 2 as #13 was fabricated as follows. A mixture was prepared from the following elements of the indicated purities: titanium, 99.9%; nickel, 99.99%; platinum, 99.99%; iron, 99.95% and zirconium, 99.99%. The mixture weight was 50 g and it contained 16.188 grams of titanium, 11.905 grams of nickel, 19.780 grams of platinum, 1.510 grams of iron and 0.617 gram of zirconium, which corresponds to the composition: 50.0 at. % Ti; 30.0 at. % Ni; 15.0 at. % Pt; 4.0 at. % Fe; and 1.0 at. % Zr ($Ti_{50.0}Ni_{30.0}Pt_{15.0}Fe_{4.0}Zr_{1.0}$).

Similar to the previous example, the mixture was molten in an arc furnace in a purified argon atmosphere (about 0.4 atm Ar) at a temperature of about 1300° C. in a water-cooled copper mold. The arc current was 500 A. Once all the components were melted, the arc was maintained for one additional minute, and then the arc was switched off. The melt was then cooled to a temperature of about 40° C. To improve the homogeneity of the alloy, the ingot was remelted six times. After cooling between each remelt, the ingot was turned upside down.

For measurements of mechanical properties (i.e., to obtain $\sigma(\epsilon)$ curves), bars having a rectangular cross-section of 1.2 mm by 1.2 mm and a length of 26.0 mm were fabricated and tested as in the previous example.

Figure 11:
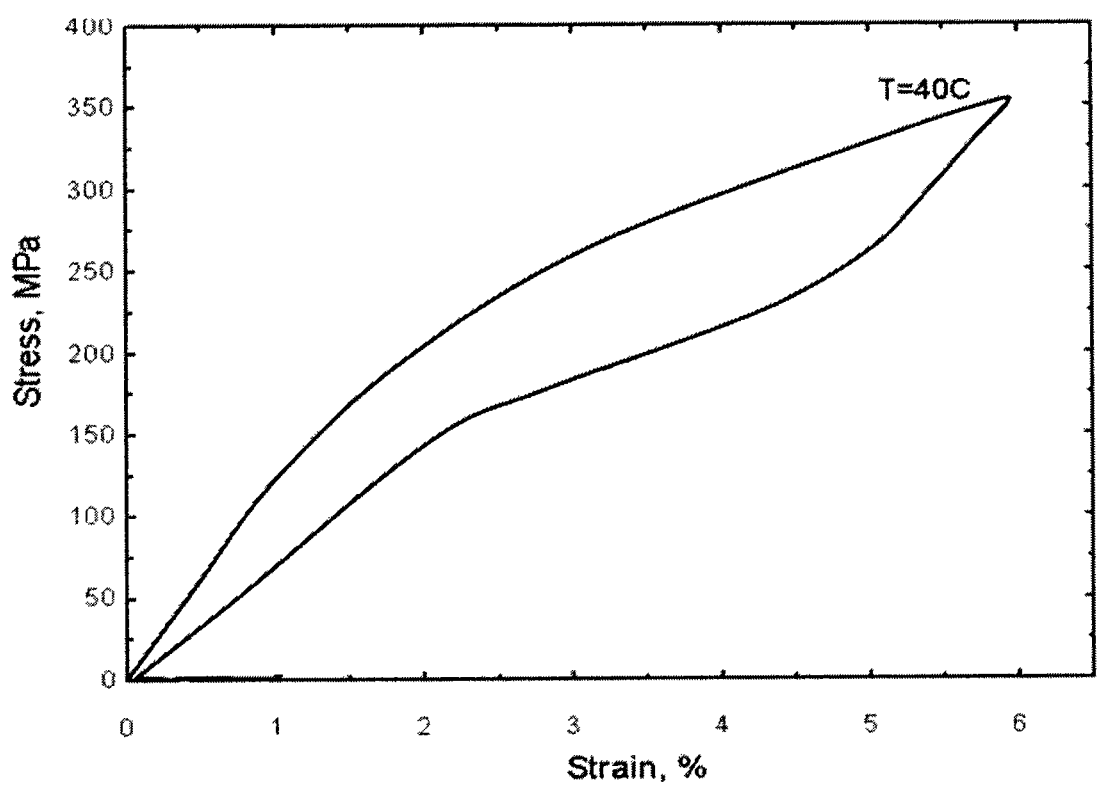
Figure 12:
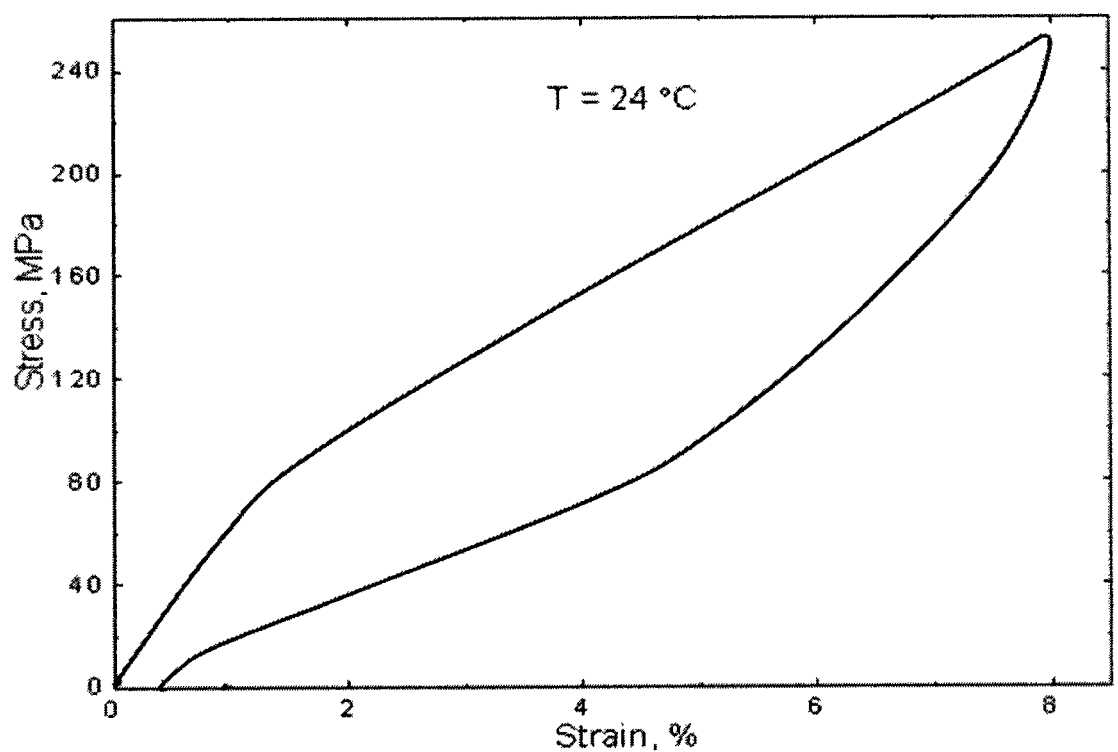

FIG. 11 illustrates a stress-strain plot for measurements at the temperature of 24° C. of a $Ti_{50.0}Ni_{30.0}Pt_{15.0}Fe_{4.0}Zr_{1.0}$ sample prepared as described above, including a further annealing at the temperature of 800° C. over 120 minutes followed by cooling to room temperature. FIG. 12 illustrates a stress-strain plot for measurements at the temperature of 40° C. of a $Ti_{50.0}Ni_{30.0}Pt_{15.0}Fe_{4.0}Zr_{1.0}$ sample prepared as described above without any further heat treatment. Both figures show a stress-strain hysteresis which is characteristic of superelastic behavior. The $Ti_{50.0}Ni_{30.0}Pt_{15.0}Fe_{4.0}Zr_{1.0}$ alloy exhibits a recoverable strain of about 7% under a torsional stress of about 250 MPa at 24° C. At 40° C., the alloy exhibits a recoverable strain of about 6% at a torsional stress of 350 MPa.

It is postulated, based on these data, that a $Ti_{50.0}Ni_{30.0}Pt_{15.0}Fe_{4.0}Zr_{1.0}$ alloy having an austenite finish temperature $A_f$ of less than about 24° C. may be fabricated as described herein. Accordingly, it is concluded that superelastic behavior may be obtained at human body temperature (37° C.) from a quintary nickel-titanium alloy including platinum, iron, and zirconium and having the composition of alloy #13.

Example 2.3

The alloy designated in Table 2 as #14 was fabricated as follows. A mixture was prepared from the following elements of the indicated purities: titanium, 99.9%; nickel, 99.99%; gold, 99.95%; iron, 99.95% and zirconium, 99.99%. The mixture weight was 50 g and it contained 17.761 grams of titanium, 16.548 grams of nickel, 14.607 grams of gold, 0.4970 gram of iron and 0.6765 gram of zirconium, which corresponds to the composition: 50.0 at. % Ti; 37.8 at. % Ni; 10.0 at. % Au; 1.2 at. % Fe; and 1.0 at. % Zr ($Ti_{50.0}Ni_{37.8}Au_{10.0}Fe_{1.2}Zr_{1.0}$).

As in the previous example, the mixture was molten in an arc furnace in a purified argon atmosphere (about 0.4 atm Ar) at a temperature of about 1300° C. in a water-cooled copper mold. The arc current was 500 A. Once all the components were melted, the arc was maintained for one additional minute, and then the arc was switched off. The melt was then cooled to a temperature of about 40° C. To improve the homogeneity of the alloy, the ingot was remelted six times. After cooling between each remelt, the ingot was turned upside down.

For measurements of mechanical properties (i.e., to obtain $\sigma(\epsilon)$ curves), bars having a rectangular cross-section of 1.2 mm by 1.2 mm and a length of 26.0 mm were fabricated and tested as described previously. The tests were carried out at a temperature of 23° C. and 39° C.

Table 4 below provides a summary of the recoverable strain values obtained for sample #14 from the mechanical tests. Depending on the test temperature, heat treatment, and the maximum applied stress ($\tau_{max}$), recoverable strain values ($\gamma_{resilience}$) ranging from 2.6% to 8.7% were obtained. Also given in the table is the residual plastic component of the deformation, $\gamma_{residual}$.

It is postulated, based on these data, that a superelastic $Ti_{50.0}Ni_{37.8}Au_{10.0}Fe_{1.2}Zr_{1.0}$ alloy having an austenite finish temperature $A_f$ of less than about 23° C. may be fabricated as described herein. Accordingly, it is concluded that superelastic behavior may be obtained at human body temperature (37° C.) from a quintary nickel-titanium alloy including Au, Fe, and Zr and having the composition of alloy #14.

TABLE 4

Recoverable Strain Data for Alloy #14.

| Heat Treatment | $T_{experiment}$, ° C. | $\tau_{maximum}$, MPa | $\gamma_{resilience}$, % | $\gamma_{residual}$, % |
|---|---|---|---|---|
| N/A | 23° C. | 185 | 2.6 | 0.10 |
|  |  | 205 | 3.7 | 0.15 |
|  |  | 220 | 5.0 | 0.10 |
|  |  | 232 | 7.0 | 0.15 |
| N/A | 39° C. | 215 | 4.9 | 0.10 |
|  |  | 247 | 5.5 | 0.20 |
|  |  | 270 | 7.0 | 0.30 |
|  |  | 290 | 8.7 | 0.60* |

*At a subsequent heating to a temperature higher than that of the experiment, an additional 0.15% strain recovery is observed. The residual plastic component of the deformation $\gamma_{residual}$ is 0.45% in this case.

Example 2.4

According to this example, the specimen designated as alloy #15 in Table 2 was fabricated as follows. A mixture was prepared from the following elements of the indicated purities: titanium, 99.9%; nickel, 99.99%; gold, 99.95%; and aluminum, 99.999%. The mixture weight was 50 g, and it contained 16.013 grams of titanium, 13.734 grams of nickel, 20.034 grams of gold, and 0.219 gram of aluminum which corresponds to the composition: 49.3 at. % Ti; 34.5 at. % Ni; 15.0 at. % Au; and 1.2 at. % Al ($Ti_{49.3}Ni_{34.5}Au_{15.0}Al_{1.2}$). The mixture was molten in an arc furnace in a purified argon atmosphere (about 0.4 atm Ar) at a temperature of about 1300° C. in a water-cooled copper mold. The arc current was 500 A. Once all the components were melted, the arc was maintained for one additional minute, and then the arc was switched off. The melt was then cooled to a temperature of about 40° C. To improve the homogeneity of the alloy, the ingot was remelted six times. After cooling between each remelt, the ingot was turned upside down. After the final cooling, bars having a rectangular cross-section of 1.2 mm by 1.2 mm and a length of 26.0 mm were fabricated and tested as described previously to evaluate the superelastic behavior of the alloy.

Figure 13:
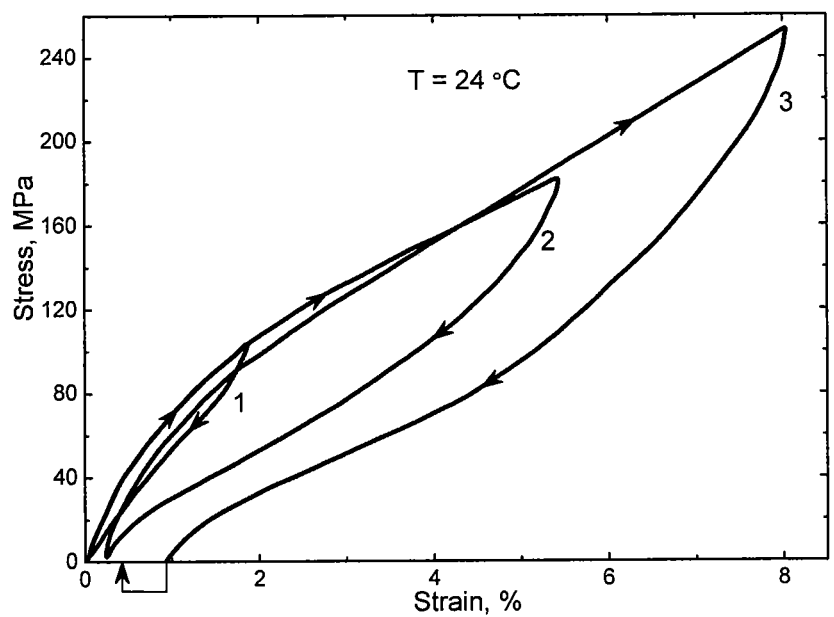

FIG. 13 illustrates a stress-strain plot for measurements at the temperature of 24° C. of a $Ti_{49.3}Ni_{34.5}Au_{15.0}Al_{1.2}$ sample prepared as described above. The sample was annealed at a temperature of 450° C. for 2 hours before the mechanical test. The plot shows a stress-strain hysteresis which is characteristic of superelastic behavior. As is apparent from the plot, the $Ti_{49.3}Ni_{34.5}Au_{15.0}A_{1.2}$ alloy achieves a recoverable strain of about 7% in response to an applied torsional stress of 255 MPa at a test temperature of 24° C.

Table 5 below provides a summary of the recoverable strain values obtained for samples #15/1 and 15/2 from the mechanical tests. Depending on the test temperature, heat treatment, and the maximum applied torsional stress ($\tau_{max}$), recoverable strain values ($\gamma_{resilience}$) in the range of from 1.9% to 7.6% were obtained for the specimens. Also given in the table is the residual plastic component of the deformation, $\gamma_{residual}$.

It is postulated, based on these data, that a superelastic $Ti_{49.3}Ni_{34.5}Au_{15.0}Al_{1.2}$ alloy having an austenite finish temperature $A_f$ of less than about 23° C. may be fabricated as described herein. Accordingly, it is concluded that superelastic behavior may be obtained at human body temperature (37° C.) from a quaternary nickel-titanium alloy including gold and aluminum and having the composition of alloy #15.

TABLE 5

Recoverable Strain Data for Alloy #15

| Alloy | Heat Treatment | $T_{experiment}$, ° C. | $\tau_{maximum}$, MPa | $\gamma_{resilience}$, % | $\gamma_{residual}$, % |
|---|---|---|---|---|---|
| 15/1 | As-cast; no heat treatment | 23 | 150 | 3.10 | 0.10 |
| | | | 215 | 5.80 | 0.40 |
| | | 80 | 190 | 2.3 | ≤0.10 |
| | | | 275 | 4.8 | 0.65 |
| | Annealed at 450° C. for 2 hours and water quenched | 24 | 105 | 1.9 | 0 |
| | | | 182 | 5.3 | 0.20 |
| | | | 255 | 7.0 | 0.7 |
| | | 36 | 226 | 6.0 | 0.4 |
| | | | 205 | 5.2 | 0.15 |
| | | 120 | 180 | 2.0 | ≤0.10 |
| | | | 290 | 3.4 | 0.30 |
| 15/2 | Annealed at 450° C. for 2 hours and water quenched | 37 | 190 | 5.45 | 0.15 |
| | | | 230 | 6.5 | 0.40 |
| | | | 295 | 7.55 | 1.25* |

*At a subsequent heating at a temperature higher than that of the experiment, an additional 1.15% strain was recovered. The residual plastic component of the deformation $\gamma_{residual}$ is 0.1% in this case.

Example 2.5

According to this example, the specimen designated as alloy #16 in Table 2 was fabricated as follows. A mixture was prepared from the following elements of the indicated purities: titanium, 99.9%; nickel, 99.99%; gold, 99.95%; and chromium, 99.9%%. The mixture weight was 50 g, and it contained 16.257 grams of titanium, 13.416 grams of nickel, 19.975 grams of gold, and 0.351 gram of chromium which corresponds to the composition: 50.2 at. % Ti; 33.8 at. % Ni; 15.0 at. % Au; and 1.0 at. % Cr ($Ti_{50.2}Ni_{33.8}Au_{15.0}Cr_{1.0}$). The mixture was molten in an arc furnace in a purified argon atmosphere (about 0.4 atm Ar) at a temperature of about 1300° C. in a water-cooled copper mold. The arc current was 500 A. Once all the components were melted, the arc was maintained for approximately one additional minute, and then the arc was switched off. The melt was then cooled to a temperature of about 40° C. To improve the homogeneity of the alloy, the ingot was remelted six times. After cooling between each remelt, the ingot was turned upside down. After the final cooling, bars having a rectangular cross-section of 1.2 mm by 1.2 mm and a length of 26.0 mm were fabricated and tested as described previously to evaluate the superelastic behavior of the alloy.

Figure 14:
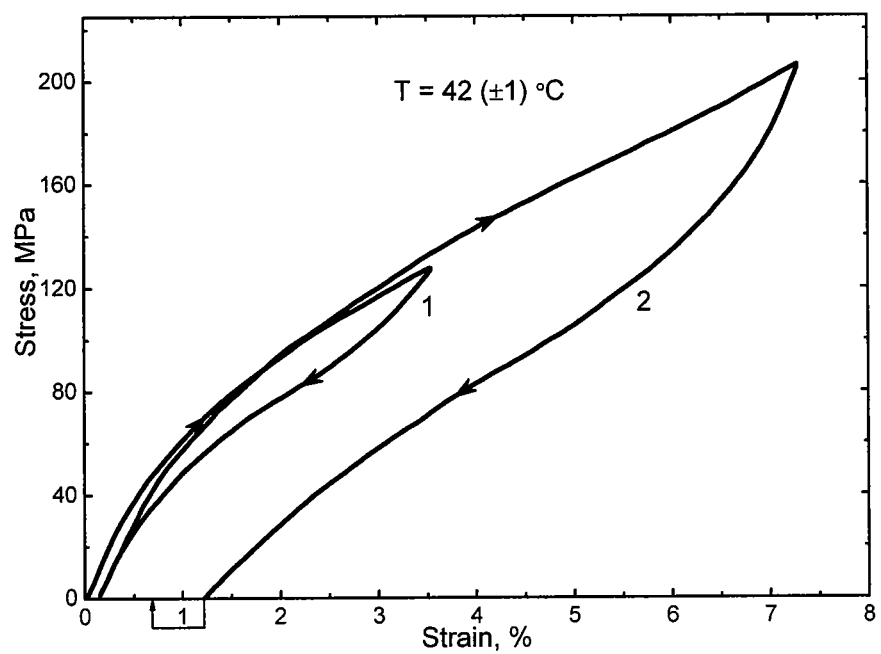

FIG. 14 illustrates a stress-strain plot for measurements at the temperature of 24° C. of a $Ti_{50.2}Ni_{33.8}Au_{15.0}Cr_{1.0}$ sample prepared as described above. The sample was annealed at a temperature of 800° C. for 1 hour and slow-cooled with the furnace before the mechanical test. The plot shows a stress-strain hysteresis which is characteristic of superelastic behavior. As is apparent from the plot, the $Ti_{50.2}Ni_{33.8}Au_{15.0}Cr_{1.0}$ alloy achieves a recoverable strain of 6.1% in response to the applied torsional stress of 205 MPa at a test temperature of 42° C.

Table 6 below provides a summary of the recoverable strain values obtained for samples #16 from the stress-strain tests. Depending on the test temperature, heat treatment, and the maximum applied torsional stress ($\tau_{max}$), recoverable strain values ($\gamma_{resilience}$) in the range of from 2.9% to 5.6% were obtained for the alloy. Also given in the table is the residual plastic component of the deformation, $\gamma_{residual}$.

It is postulated, based on these data, that a superelastic $Ti_{50.2}Ni_{33.8}Au_{15.0}Cr_{1.0}$ alloy having an austenite finish temperature $A_f$ of less than about 25° C. may be fabricated as described herein. Accordingly, it is concluded that superelastic behavior may be obtained at human body temperature (37° C.) from a quaternary nickel-titanium alloy including gold and chromium and having the composition of alloy #16.

TABLE 6

Recoverable Strain Data for Alloy #16

| Heat Treatment | $T_{experiment}$, ° C. | $\tau_{maximum}$, MPa | $\gamma_{resilience}$, % | $\gamma_{residual}$, % |
|---|---|---|---|---|
| 800° C., 1 hour, Slow cooling with furnace | 42° C. | 127 | 2.90 | 0.15 |
| | | 205 | 6.10 | 1.05* |
| | 56° C. | 172 | 3.70 | 0.05 |
| | 61° C. | 225 | 5.60 | 0.70** |
| | 102° C. | 288 | 4.05 | 0.95*** |
| | 25° C. (after tests at temperatures 42° C.-102° C.) | 110 | 3.00 | 0.25 |
| | | 187 | 5.50 | 0.70**** |

*At a subsequent heating to a temperature higher than that of the experiment, an additional strain of 0.5% was recovered. The residual plastic component of the deformation $\gamma_{residual}$ is 0.55% in this case.
**At a subsequent heating to a temperature higher than that of the experiment, an additional strain of 0.3% was recovered. The residual plastic component of the deformation $\gamma_{residual}$ is 0.4% in this case.
***At a subsequent heating to a temperature higher than that of the experiment, an additional strain of 0.1% was recovered. The residual plastic component of the deformation $\gamma_{residual}$ is 0.85% in this case.
****At a subsequent heating to a temperature higher than that of the experiment, the strain was fully recovered.

Example 3.1

Electrical resistivity experiments were carried out in an effort to determine the phase transformation temperatures (e.g., $M_s$, $M_f$, $A_s$, and $A_f$) of alloys 4, 13, 14, 15 and 16. Samples of 15.0 mm by 1.0 mm by 1.0 mm in size were cut from the ingots by electrodischarge machining for the measurements. The surfaces of the samples were mechanically polished, and then, on each side of the sample, current and potential conductors were spot welded. Measurements were carried out using the standard four-terminal method. Current wires were connected to a regulated power supply at a constant current of ~1 A, and potential conductors were connected to a terminal of a two-coordinate recorder. A thermocouple for measurement and control of the sample temperature was brought to the middle of a sample. The temperature of the device was varied from the boiling temperature of liquid nitrogen (−196° C.) to 450° C. Electroresistance measurements within a given temperature range were carried out during heating or cooling of a sample at a rate of about 2-3° C./min. All measurements were carried out in air. If the geometry of a sample was executed with sufficiently precise linear dimensions, then specific electrical resistance ρ(T) was measured; otherwise, the relative change of electroresistance was determined. Transformation temperatures determined from the electrical resistivity data are presented in Table 7 below for alloy samples 4, 13 and 16 as a function of heat treatment.

Based on plots of the electrical resistivity data, an austenite finish temperature $A_f$ of about 21° C. was obtained for alloy 13, and alloy 16 exhibited values of $A_f$ of less than human body temperature (37° C.) for three different heat treatment conditions, as indicated in Table 7. Alloy 4 exhibited $A_f$ values of 94° C. and 96° C. in the as-cast and annealed states (see Table 7), although for some heat treatment conditions, no phase transformations were observed during the resistivity measurements. Alloy 15 also showed no phase transformations during resistivity experiments conducted on as-cast (15/1) and annealed (15/2) samples. A portion of alloy 14 appeared to undergo a phase transformation in the range of −90° C. to 0° C.; however, no phase transformations were observed in the main volume of alloy 14, which was studied in the as-cast state.

TABLE 7

Transformation Temperatures Determined from Electrical Resistivity Measurements

| | Thermal treatment | $M_f$ (° C.) | $M_s$ (° C.) | $A_s$ (° C.) | $A_f$ (° C.) |
|---|---|---|---|---|---|
| Alloy #4 | As-cast; no thermal treatment | −50 | 68 | −10 | 94 |
| | Annealed at 800° C. for 1.5 hours, slow cooled with furnace + annealed at 450° C. for 70 min and water quenched | −20 | 65 | 20 | 96 |
| Alloy #13 | As-cast; no thermal treatment | −100 | −27 | −67 | 21 |
| Alloy #16 | As-cast; no thermal treatment | −42 | 62 | −18 | 72 |
| | As-cast and aged at 330° C. for 150 min. | −35 | 56 | −24 | 63 |
| | As-cast and aged at 330° C. for 150 min. + aged at 450° C. for 2 hours | −36 | 60 | −11 | 71 |
| | Annealed at 800° C. for 1.5 hours | −50 | 11 | −31 | 19 |
| | Annealed at 800° C. for 1.5 hours + aged at 330° C. for 155 min. | −57 | 12 | −29 | 20 |
| | Annealed at 800° C. for 1.5 hours + aged at 330° C. for 155 min + aged at 450° C. for 2 hours | −48-(−38) | 35 | 10-15 | 42 |
| | Annealed at 800° C. for 1.5 hours + aged at 330° C. for 155 min + aged at 450° C. for 2 hours + aged at 330° C. for 2 hours (furnace cooled) | −57 | 17 | −49 | 27 |
| | Annealed at 800° C. for 1.5 hours + aged at 330° C. for 155 min + aged at 450° C. for 2 hours + aged at 330° C. for 2 hours (furnace cooled) + aged at 500° C. for 1.5 hours | −32 | 41 | −23 | 47 |

Example 4.1

Figure 7:
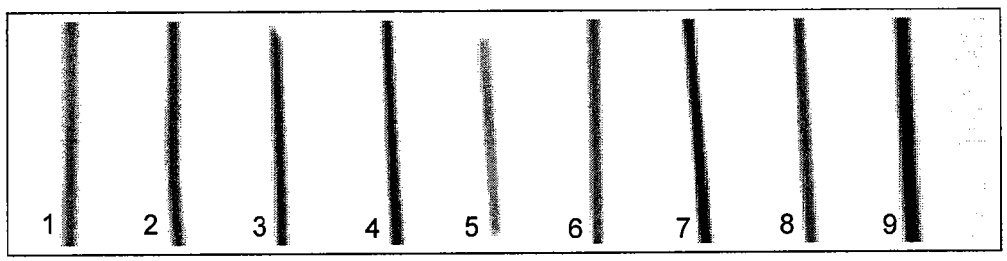
FIG. 7 illustrates the comparative contrast of x-ray pictures of exemplary wire samples.

The radiopacity of wire samples made from the alloys can be evaluated by using, for example, an x-ray device such as a Siemens Coroskop Plus/T.O.P. Referring to FIG. 7, exemplary x-ray photographs of wires having a diameter of 400 micrometers made from various Ti—Ni based alloys containing various radiopaque elements are illustrated. Specifically, FIG. 7 illustrates the comparative contrast of x-ray pictures of wire samples made from the TiNiMe alloy having different concentrations of radiopaque elements Me, such as palladium—10 at. % (sample 1); palladium—25 at. % (sample 2); palladium—30 at. % (sample 3); palladium—35 at. % (sample 4); gold—8 at. % (sample 5), gold—14 at. % (sample 6), gold—35 at. % (sample 7); platinum—12 at. % (sample 8), platinum—35 at. % (sample 9). As can be seen, the higher the concentration of the radiopaque element, the higher is the contrast of the x-ray pictures.

Figure 8:
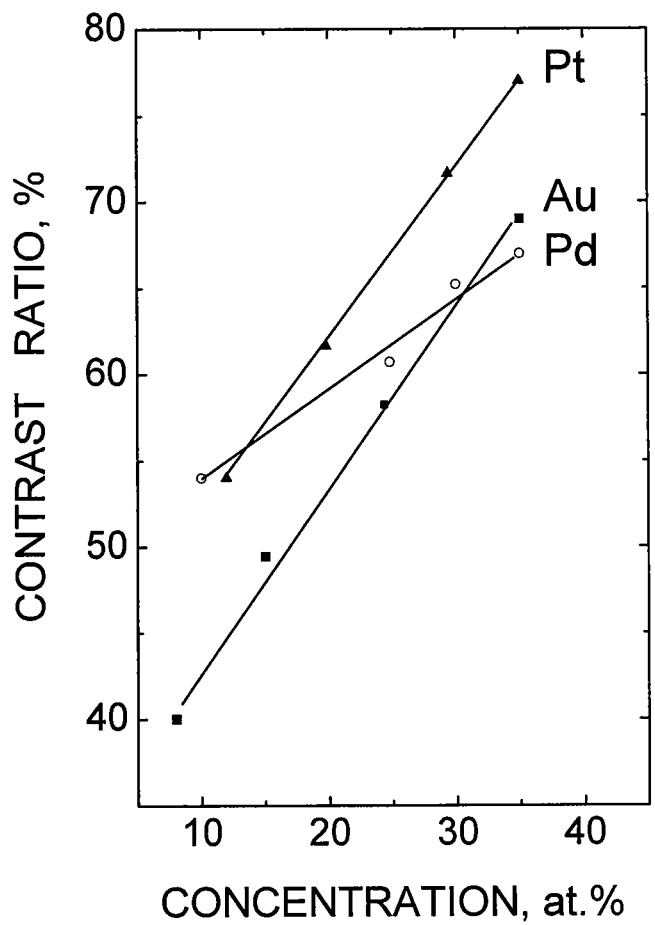
FIG. 8 illustrates the dependence of the relative contrast of the x-ray pictures shown in FIG. 7 on the amount of the radiopaque alloying elements.

A quantitative evaluation of the contrast (on the gray scale) of the x-ray pictures can be made with, for example, the use of a graphics editor such as <<Adobe Photoshop-7.0>>. FIG. 8 illustrates the dependence of the relative contrast of the x-ray pictures shown in FIG. 7 on the amount of the radiopaque alloying element. As can be seen in FIG. 8, if the content of the radiopaque alloying element in the alloy is greater than 15 atomic percent, the radiopacity of the samples increases by more than 50% when compared to the binary $Ti_{50.0}Ni_{50.0}$ alloy.

Figure 15:
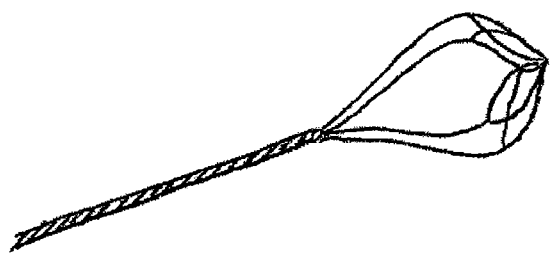
FIG. 15 illustrates an exemplary medical device including the radiopaque alloy according to one embodiment.

Various articles can be manufactured from the radiopaque alloy of the present invention. In particular, the alloy can be utilized for manufacturing medical devices. At least one component of the medical device may comprise the alloy. The component may have the form of a wire, a tube (i.e., "cannula") or another cast or worked shape, such as a ribbon, button, bar, rivet, sphere, disk, sheet, or foil. Examples of the medical devices that may utilize the radiopaque alloy include, but are not limited to, guide wires, cardiac pacing leads, sutures, prosthetic implants, stents, stent grafts, intraluminal filters, retrieval baskets, graspers, snares, radiopaque markers or marker bands, torqueable catheters, introducer sheaths, aneurysm clips, bone plates and screws, femoral fixation devices, intrauterine contraceptive devices, intramedullary nails and pins, and joints for ankles, elbows, fingers, knees, hips, etc. An exemplary medical device, in particular, a retrieval basket, including at least one component formed of the radiopaque alloy is shown schematically in FIG. 15.

It should be appreciated that the application field of the alloy of the present invention is not limited to medicine. The alloy can also be used for making thermo-sensitive actuating load-bearing elements and other constructions in instrument-making and radio-electronics, etc.

As such, those skilled in the art to which the present invention pertains, can appreciate that while the present invention has been described in terms of preferred embodiments, the concept upon which this disclosure is based may readily be utilized as a basis for the designing of other structures, systems and processes for carrying out the several purposes of the present invention.

Also, it is to be understood that the phraseology and terminology employed herein are for the purpose of description and should not be regarded as limiting.

Finally, it should be noted that the word "comprising" as used throughout the appended claims is to be interpreted to mean "including but not limited to."

It is important, therefore, that the scope of the invention is not construed as being limited by the illustrative embodiments set forth herein. Other variations are possible within the scope of the present invention as defined in the appended claims. Other combinations and sub-combinations of features, functions, elements and/or properties may be claimed through amendment of the present claims or presentation of new claims in this or a related application. Such amended or new claims, whether they are directed to different combinations or directed to the same combinations, whether different, broader, narrower or equal in scope to the original claims, are also regarded as included within the subject matter of the present description.

The invention claimed is:

1. A radiopaque alloy having shape memory and superelastic properties, consisting of:
   titanium at a concentration of from about 48 to about 52 atomic percent;
   at a concentration of from about 10 to about 35 atomic percent;
   at least one additional alloying element selected from the group consisting of iron and cobalt at a concentration of from about 0.5 to about 8 atomic percent;
   at least one further alloying element selected from the group consisting of aluminum, chromium, and zirconium at a concentration of from about 0.5 to about 4 atomic percent; and
   nickel and inevitable impurities as a balance.

2. The alloy of claim 1, wherein the nickel has a concentration of from about 29 at. % to about 52 at. %.

3. The alloy of claim 1, wherein the alloy comprises:
   gold at a concentration of about 20 at. %;
   iron at a concentration of about 0.5 at. %; and
   zirconium at a concentration of about 1 at. %.

4. The alloy of claim 1, wherein the alloy comprises:
   gold at a concentration of about 10 at. %;
   iron at a concentration of about 1.2 at. %; and
   zirconium at a concentration of about 1 at. %.

5. The alloy of claim 1, wherein the alloy comprises:
   gold at a concentration of about 15 at. %; and
   aluminum at a concentration of about 1.2 at. %.

6. The alloy of claim 1, wherein the alloy comprises:
   gold at a concentration of about 15 at. %; and
   chromium at a concentration of about 1 at. %.

7. The alloy of claim 1, wherein the recoverable strain is at least about 5%.

8. The alloy of claim 1, wherein the alloy is superelastic and has an austenite finish temperature at or below 37° C.

9. A medical device comprising at least one component comprising the radiopaque alloy of claim 1.

10. The medical device of claim 9, wherein the component comprises at least one of a wire and a cannula made of the radiopaque alloy.

* * * * *

UNITED STATES PATENT AND TRADEMARK OFFICE
CERTIFICATE OF CORRECTION

PATENT NO. : 8,801,875 B2
APPLICATION NO. : 12/336120
DATED : August 12, 2014
INVENTOR(S) : Valery Diamant et al.

Page 1 of 1

It is certified that error appears in the above-identified patent and that said Letters Patent is hereby corrected as shown below:

In the Claims

In column 25, line 13, before "at a concentration of from about 10 to about 35 atomic percent" insert --gold--.

Signed and Sealed this
Third Day of February, 2015

Michelle K. Lee
*Deputy Director of the United States Patent and Trademark Office*